(12) United States Patent
Zhou et al.

(10) Patent No.: US 9,902,772 B2
(45) Date of Patent: Feb. 27, 2018

(54) ANTIBODY THERAPEUTICS THAT BIND LAG3

(71) Applicant: Sorrento Therapeutics, Inc., San Diego, CA (US)

(72) Inventors: Heyue Zhou, San Diego, CA (US); John Dixon Gray, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 20 days.

(21) Appl. No.: 15/217,238

(22) Filed: Jul. 22, 2016

(65) Prior Publication Data

US 2017/0022273 A1    Jan. 26, 2017

Related U.S. Application Data

(60) Provisional application No. 62/195,651, filed on Jul. 22, 2015.

(51) Int. Cl.
*C07K 16/30* (2006.01)
*C07K 16/28* (2006.01)

(52) U.S. Cl.
CPC .......... *C07K 16/2803* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3069* (2013.01); C07K 2317/21 (2013.01); C07K 2317/33 (2013.01); C07K 2317/55 (2013.01); C07K 2317/622 (2013.01); C07K 2317/70 (2013.01); C07K 2317/76 (2013.01); C07K 2317/92 (2013.01)

(58) Field of Classification Search
None
See application file for complete search history.

(56) References Cited

U.S. PATENT DOCUMENTS

| | | |
|---|---|---|
| 9,505,839 B2 * | 11/2016 | Lonberg ............. C07K 16/2803 |
| 2004/0142382 A1 | 7/2004 | Veldman et al. |
| 2005/0220795 A1 | 10/2005 | Wittrup et al. |
| 2009/0104204 A1 | 4/2009 | Throsby et al. |
| 2013/0011406 A1 | 1/2013 | Hadari et al. |
| 2013/0323248 A1 | 12/2013 | Gros et al. |
| 2014/0093511 A1 | 4/2014 | Lonberg et al. |
| 2014/0294827 A1 | 10/2014 | Gastwirt et al. |
| 2014/0349349 A1 | 11/2014 | Dauner et al. |

OTHER PUBLICATIONS

International Search Report and Written Opinion for International Application No. PCT/US2016/043562 dated Jan. 12, 2017.

* cited by examiner

*Primary Examiner* — Laura B Goddard
*Assistant Examiner* — Meera Natarajan
(74) *Attorney, Agent, or Firm* — Womble Bond Dickinson (US) LLP; Danielle L. Herritt

(57) ABSTRACT

There is disclosed compositions and methods relating to or derived from anti-LAG3 antibodies. More specifically, there is disclosed fully human antibodies that bind LAG3, LAG3-antibody binding fragments and derivatives of such antibodies, and LAG3-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease.

10 Claims, 6 Drawing Sheets

ANTIBODY THERAPEUTICS THAT BIND LAG3

RELATED APPLICATIONS

This application claims priority to U.S. Provisional Application No. 62/195,651 filed on Jul. 22, 2015, the entire contents of which are incorporated by reference in their entirety herein.

SEQUENCE LISTING

The instant application contains a Sequence Listing which has been submitted electronically in ASCII format and is hereby incorporated by reference in its entirety. Said ASCII copy, created on Jul. 20, 2016, is named 126036-04702_SL.txt and is 21,129 bytes in size.

TECHNICAL FIELD

The present disclosure provides compositions and methods relating to or derived from anti-LAG3 antibodies. More specifically, the present disclosure provides fully human antibodies that bind LAG3, LAG3-antibody binding fragments and derivatives of such antibodies, and LAG3-binding polypeptides comprising such fragments. Further still, the present disclosure provides antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating a disease.

BACKGROUND

Lymphocyte Activation Gene-3, or LAG3 (also known as CD223), is a member of the immunoglobulin supergene family and is structurally and genetically related to CD4. LAG3 is not expressed on resting peripheral blood lymphocytes but is expressed on activated T cells and NK cells. LAG3 is a membrane protein encoded by a gene located on the distal part of the short arm of chromosome 12, near the CD4 gene, suggesting that the LAG3 gene may have evolved through gene duplication (Triebel et al. (1990) *J. Exp. Med.* 171:1393-1405).

Similar to CD4, LAG3 has been demonstrated to interact with MHC Class II molecules but, unlike CD4, LAG3 does not interact with the human immunodeficiency virus gp120 protein (Baixeras et al. (1992) *J. Exp. Med.* 176:327-337). Studies using a soluble LAG3 immunoglobulin fusion protein (sLAG3Ig) demonstrated direct and specific binding of LAG3 to MHC class II on the cell surface (Huard et al. (1996) *Eur. J. Immunol.* 26:1180-1186).

In in vitro studies of antigen-specific T cell responses, the addition of anti-LAG3 antibodies led to increased T cell proliferation, higher expression of activation antigens such as CD25, and higher concentrations of cytokines such as interferon-gamma and interleukin-4, supporting a role for the LAG3/MHC class II interaction in down-regulating antigen-dependent stimulation of CD4$^+$ T lymphocytes (Huard et al. (1994) *Eur. J. Immunol.* 24:3216-3221). The intra-cytoplasmic region of LAG3 has been demonstrated to interact with a protein termed LAP, which is thought to be a signal transduction molecule involved in the downregulation of the CD3/TCR activation pathway (Iouzalen et al. (2001) *Eur. J. Immunol.* 31:2885-2891). Furthermore, CD4$^+$ CD25$^+$ regulatory T cells ($T_{reg}$) have been shown to express LAG3 upon activation and antibodies to LAG3 inhibit suppression by induced $T_{reg}$ cells, both in vitro and in vivo, suggesting that LAG3 contributes to the suppressor activity of $T_{reg}$ cells (Huang, C. et al. (2004) *Immunity* 21:503-513). Still further, LAG3 has been shown to negatively regulate T cell homeostasis by regulatory T cells in both T cell-dependent and independent mechanisms (Workman and Vignali (2005) *J. Immunol.* 174:688-695).

In certain circumstances, LAG3 also has been shown to have immunostimulatory effects. For example, LAG3 transfected tumor cells transplanted into syngeneic mice showed growth reduction or complete regression as compared to untransfected tumor cells, suggesting that LAG3 expression on the tumor cells stimulated an anti-tumor response by triggering antigen LAG3 presenting cells via MHC class II molecules (Prigent et al. (1999) *Eur. J. Immunol.* 29:3867-3876). Additionally, soluble LAG3 Ig fusion protein has been shown to stimulate both humoral and cellular immune responses when administered to mice together with an antigen, indicating that soluble LAG3Ig can function as a vaccine adjuvant (El Mir and Triebel (2000) *J. Immunol.* 164:5583-5589). Furthermore, soluble human LAG3Ig has been shown to amplify in vitro generation of type I tumor-specific immunity (Casati et al. (2006) *Cancer Res.* 66:4450-4460). The functional activity of LAG3 is reviewed further in Triebel (2003) *Trends Immunol.* 24:619-622. In view of the above, additional agents for modulating the activity of LAG3 are of interest.

SUMMARY OF THE INVENTION

The present invention provides novel anti-human LAG3 (hLAG3) antibodies and fragments thereof. The present invention relates to anti-LAG3 antibodies that are advantageous, for example, in that they can act as immune checkpoint inhibitors and may be used in immunotherapy for treating disorders such as cancer.

In one embodiment, the present disclosure provides a fully human antibody of an IgG class that binds to a LAG3 epitope with a binding affinity of at least 10$^{-6}$ M, which has a heavy chain variable domain sequence that is at least 95% identical to an amino acid sequence selected from the group consisting of SEQ ID NO. 1, SEQ ID NO. 8, SEQ ID NO. 10, SEQ ID NO. 12, and combinations thereof, and has a light chain variable domain sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof. In one embodiment, the fully human antibody has both a heavy chain and a light chain wherein the antibody has a heavy chain/light chain variable domain sequence selected from the group consisting SEQ ID NO. 1/SEQ ID NO. 2 (called L35D4 herein), SEQ ID NO. 1/SEQ ID NO. 3 (called L35G6 herein), SEQ ID NO. 1/SEQ ID NO. 4 (called L33H11 herein), SEQ ID NO. 1/SEQ ID NO. 5 (called L32A9 herein), SEQ ID NO. 1/SEQ ID NO. 6 (called L32D10 herein), SEQ ID NO. 1/SEQ ID NO. 7 (called L32A4 herein), SEQ ID NO. 8/SEQ ID NO. 9 (called L3A1 herein), SEQ ID NO. 10/SEQ ID NO. 11 (called L3A10 herein), SEQ ID NO. 12/SEQ ID NO. 13 (called L3C5 herein), SEQ ID NO. 8/SEQ ID NO. 14 (called L3E3 herein), and combinations thereof.

In one embodiment, the present disclosure provides a Fab fully human antibody fragment, having a variable domain region from a heavy chain and a variable domain region from a light chain, wherein the heavy chain variable domain sequence is at least 95% identical to an amino acid sequence selected from the group consisting of SEQ ID NO. 1, SEQ ID NO. 8, SEQ ID NO. 10, SEQ ID NO. 12, and combinations thereof, and has a light chain variable domain sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof. In one embodiment, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, and SEQ ID NO. 8/SEQ ID NO. 14, and combinations thereof.

In one embodiment, the present disclosure provides a single chain human antibody, having a variable domain region from a heavy chain and a variable domain region from a light chain and a peptide linker connecting the heavy chain and light chain variable domain regions, wherein the heavy chain variable domain sequence is at least 95% identical to an amino acid sequence selected from the group consisting of SEQ ID NO. 1, SEQ ID NO. 8, SEQ ID NO. 10, SEQ ID NO. 12, and has the light chain variable domain sequence is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof. In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, and SEQ ID NO. 8/SEQ ID NO. 14, and combinations thereof.

In one embodiment, the present disclosure further provides a method for treating a broad spectrum of mammalian cancers, infectious diseases or autoimmune reactions, comprising administering an anti-LAG3 polypeptide, wherein the fully human antibody has a heavy chain variable domain sequence that is at least 95% identical to an amino acid sequence selected from the group consisting of SEQ ID NO. 1, SEQ ID NO. 8, SEQ ID NO. 10, SEQ ID NO. 12, and combinations thereof, and has a light chain variable domain sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof.

In one embodiment, the Fab fully human antibody fragment has the heavy chain variable domain sequence that is at least 95% identical to an amino acid sequence selected from the group consisting of SEQ ID NO. 1, SEQ ID NO. 8, SEQ ID NO. 10, SEQ ID NO. 12, and combinations thereof, and has the light chain variable domain sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof.

In one embodiment, the single chain human antibody has a heavy chain variable domain sequence that is at least 95% identical to an amino acid sequence selected from the group consisting of SEQ ID NO. 1, SEQ ID NO. 8, SEQ ID NO. 10, SEQ ID NO. 12, and combinations thereof, and has a light chain variable domain sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof.

In one embodiment, the fully human antibody has both a heavy chain variable domain region and a light chain variable domain region, wherein the antibody has a heavy chain/light chain variable domain sequence selected from the group consisting of SEQ ID NO. 1/SEQ ID NO. 2 (called L35D4 herein), SEQ ID NO. 1/SEQ ID NO. 3 (called L35G6 herein), SEQ ID NO. 1/SEQ ID NO. 4 (called L33H11 herein), SEQ ID NO. 1/SEQ ID NO. 5 (called L32A9 herein), SEQ ID NO. 1/SEQ ID NO. 6 (called L32D10 herein), SEQ ID NO. 1/SEQ ID NO. 7 (called L32A4 herein), SEQ ID NO. 8/SEQ ID NO. 9 (called L3A1 herein), SEQ ID NO. 10/SEQ ID NO. 11 (called L3A10 herein), SEQ ID NO. 12/SEQ ID NO. 13 (called L3C5 herein), SEQ ID NO. 8/SEQ ID NO. 14 (called L3E3 herein), and combinations thereof. In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, SEQ ID NO. 8/SEQ ID NO. 14, and combinations thereof.

In one embodiment, the broad spectrum of mammalian cancers, infectious diseases, or autoimmune reactions to be treated is selected from the group consisting of non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML) non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and solid tumors, wherein solid tumors are selected from the group consisting of breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

In one embodiment, the invention provides an isolated fully human antibody of an IgG class that binds to a LAG3 epitope, said antibody comprising: a heavy chain variable domain sequence that is at least 95% identical to an amino acid sequence selected from the group consisting of SEQ ID NO. 1, SEQ ID NO. 8, SEQ ID NO. 10, and SEQ ID NO.

12; and a light chain variable domain sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14.

In one embodiment, the fully human antibody comprises a heavy chain/light chain variable domain sequence selected from the group consisting of SEQ ID NO. 1/SEQ ID NO. 2 (L35D4), SEQ ID NO. 1/SEQ ID NO. 3 (L35G6), SEQ ID NO. 1/SEQ ID NO. 4 (L33H11), SEQ ID NO. 1/SEQ ID NO. 5 (L32A9), SEQ ID NO. 1/SEQ ID NO. 6 (L32D10), SEQ ID NO. 1/SEQ ID NO. 7 (L32A4), SEQ ID NO. 8/SEQ ID NO. 9 (L3A1), SEQ ID NO. 10/SEQ ID NO. 11 (L3A10), SEQ ID NO. 12/SEQ ID NO. 13 (L3C5), and SEQ ID NO. 8/SEQ ID NO. 14 (L3E3).

In one embodiment, the invention features an anti-LAG3 fully human antibody Fab fragment, comprising a heavy chain variable domain sequence that is at least 95% identical to an amino acid sequence selected from the group consisting of SEQ ID NO. 1, SEQ ID NO. 8, SEQ ID NO. 10, and SEQ ID NO. 12; and comprising a light chain variable domain sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, and SEQ ID NO. 14. In one embodiment, the fully human antibody Fab fragment comprises a heavy chain/light chain variable domain sequence selected from the group consisting of SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, and SEQ ID NO. 8/SEQ ID NO. 14.

In one embodiment, the present invention provides an anti-LAG3 single chain human antibody comprising a heavy chain variable domain and a light chain variable domain which are connected by a peptide linker, wherein the heavy chain variable domain comprises an amino acid sequence that is at least 95% identical to an amino acid sequence selected from the group consisting of SEQ ID NO. 1, SEQ ID NO. 8, SEQ ID NO. 10, and SEQ ID NO. 12; and the light chain variable domain comprises an amino acid sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, and SEQ ID NO. 14.

In one embodiment, the single chain fully human antibody comprises a heavy chain/light chain variable domain sequence selected from the group consisting of SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, and SEQ ID NO. 8/SEQ ID NO. 14.

In one embodiment, the invention provides an isolated anti-human LAG3 (hLAG3) antibody, or an antigen-binding fragment thereof, comprising a heavy chain variable domain comprising complementarity determining regions (CDRs) as set forth in the heavy chain variable domain amino acid sequence selected from the group consisting of SEQ ID NO. 1, SEQ ID NO. 8, SEQ ID NO. 10, and SEQ ID NO. 12; and comprising a light chain variable domain comprising CDRs as set forth in a light chain variable region amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, and SEQ ID NO. 14. In one embodiment, the heavy chain variable domain comprises an amino acid sequence that is at least 95% identical to an amino acid sequence selected from the group consisting of SEQ ID NO. 1, SEQ ID NO. 8, SEQ ID NO. 10, and SEQ ID NO. 12; and comprises a light chain variable domain comprising an amino acid sequence that is at least 95% identical to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14. In one embodiment, the heavy chain variable domain comprises an amino acid sequence selected from the group consisting of SEQ ID NO. 1, SEQ ID NO. 8, SEQ ID NO. 10, and SEQ ID NO. 12; and comprises a light chain variable domain comprising an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14.

In another embodiment, the present invention features an isolated anti-human LAG3 (hLAG3) antibody, or an antigen-binding fragment thereof, comprising a heavy chain variable domain comprising a heavy chain CDR set (CDR1, CDR2, and CDR3) selected from the group consisting of SEQ ID Nos: 15, 16, and 17; SEQ ID Nos: 36, 37, and 38; SEQ ID Nos: 42, 43, and 44; and SEQ ID Nos: 48, 49, and 50; and a light chain variable domain comprising a light chain CDR set (CDR1, CDR2, and CDR3) selected from the group consisting of SEQ ID Nos: 18, 19, and 20; SEQ ID Nos: 21, 22, and 23; SEQ ID Nos: 24, 25, and 26; SEQ ID Nos: 27, 28, and 29; SEQ ID Nos: 30, 31, and 32; SEQ ID Nos: 33, 34, and 35; SEQ ID Nos: 39, 40, and 41; SEQ ID Nos: 45, 46, and 47; SEQ ID Nos: 51, 52, and 53; and SEQ ID Nos: 54, 55, and 56.

In one embodiment, the antibody comprises a heavy chain CDR set/light chain CDR set selected from the group consisting of the heavy chain variable domain CDR set of SEQ ID Nos: 15, 16, and 17, and the light chain variable domain CDR set of 18, 19, and 20; the heavy chain variable domain CDR set of SEQ ID Nos: 15, 16, and 17, and the light chain variable domain CDR set of 21, 22, and 23; the heavy chain variable domain CDR set of SEQ ID Nos: 15, 16, and 17, and the light chain variable domain CDR set of 24, 25, and 26; the heavy chain variable domain CDR set of SEQ ID Nos: 15, 16, and 17, and the light chain variable domain CDR set of 27, 28, and 29; the heavy chain variable domain CDR set of SEQ ID Nos: 15, 16, and 17, and the light chain variable domain CDR set of 30, 31, and 32; the heavy chain variable domain CDR set of SEQ ID Nos: 15, 16, and 17, and the light chain variable domain CDR set of 33, 34, and 35; the heavy chain variable domain CDR set of SEQ ID Nos: 36, 37, and 38, and the light chain variable domain CDR set of 39, 40, and 41; the heavy chain variable domain CDR set of SEQ ID Nos: 42, 43, and 44, and the light chain variable domain CDR set of 45, 46, and 47; the heavy chain variable domain CDR set of SEQ ID Nos: 48, 49, and 50, and the light chain variable domain CDR set of 51, 52, and 53; and the heavy chain variable domain CDR set of SEQ ID Nos: 36, 37, and 38, and the light chain variable domain CDR set of 54, 55, and 56.

In one embodiment, an anti-LAG3 antibody or antibody fragment may be used in a method for treating a subject having cancer, an infectious disease, or an autoimmune disease, said method comprising administering an effective amount of the anti-LAG3 antibody or antibody fragment to the subject.

In one embodiment, the cancer is selected from the group consisting of non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), chronic myeloid leukemia (CML), melanoma, renal cancer, prostate cancer, breast cancer, colon cancer, and lung cancer.

In another embodiment, the cancer is selected from the group consisting of bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancer, and cancer induced by asbestos.

In another embodiment, the cancer is metastatic cancer that expresses PD-L1.

In one embodiment, the infectious disease is selected from the group consisting of HIV, Hepatitis (A, B, & C), Influenza, Herpes, *Giardia*, Malaria, *Leishmania, Staphylococcus aureus, Pseudomonas aeruginosa*, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, and arboviral encephalitis virus.

In another embodiment, the infectious disease is selected from the group consisting of chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lyme disease bacteria.

In another embodiment, the infectious disease is selected from the group consisting of *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii*, and *Nippostrongylus brasiliensis*.

In one embodiment, the autoimmune disease is selected from the group consisting of Alzheimer's disease, allergy, asthma, celiac disease, Crohn's disease, Grave's disease, inflammatory bowel disease (IBD), lupus, multiple sclerosis, Myasthenia Gravis, polymyalgia rheumatica, rheumatoid arthritis, type I diabetes, and vasculitis.

In certain embodiments, the anti-LAG3 antibody, or antigen-binding fragment thereof, of the invention has a binding affinity ($K_D$) of at least $1\times10^{-6}$ M. In other embodiments, the antibody, or antigen-binding fragment thereof, of the invention has a $K_D$ of at least $1\times10^{-7}$ M. In other embodiments, the antibody, or antigen-binding fragment thereof, of the invention has a $K_D$ of at least $1\times10^{-8}$ M.

In certain embodiments, the antibody is an IgG1 isotype. In other embodiments, the antibody is an IgG4 isotype.

In one embodiment, the antibody, or antigen-binding fragment, described herein is recombinant. In another embodiment, the antibody, or antigen-binding fragment, described herein, is a recombinant human antibody, or antigen binding fragment of an antibody.

In one embodiment, the invention provides a pharmaceutical composition comprising an effective amount of an anti-LAG3 antibody, or antibody fragment disclosed herein, and a pharmaceutically acceptable carrier.

DETAILED DESCRIPTION

Definitions

Figure 1:
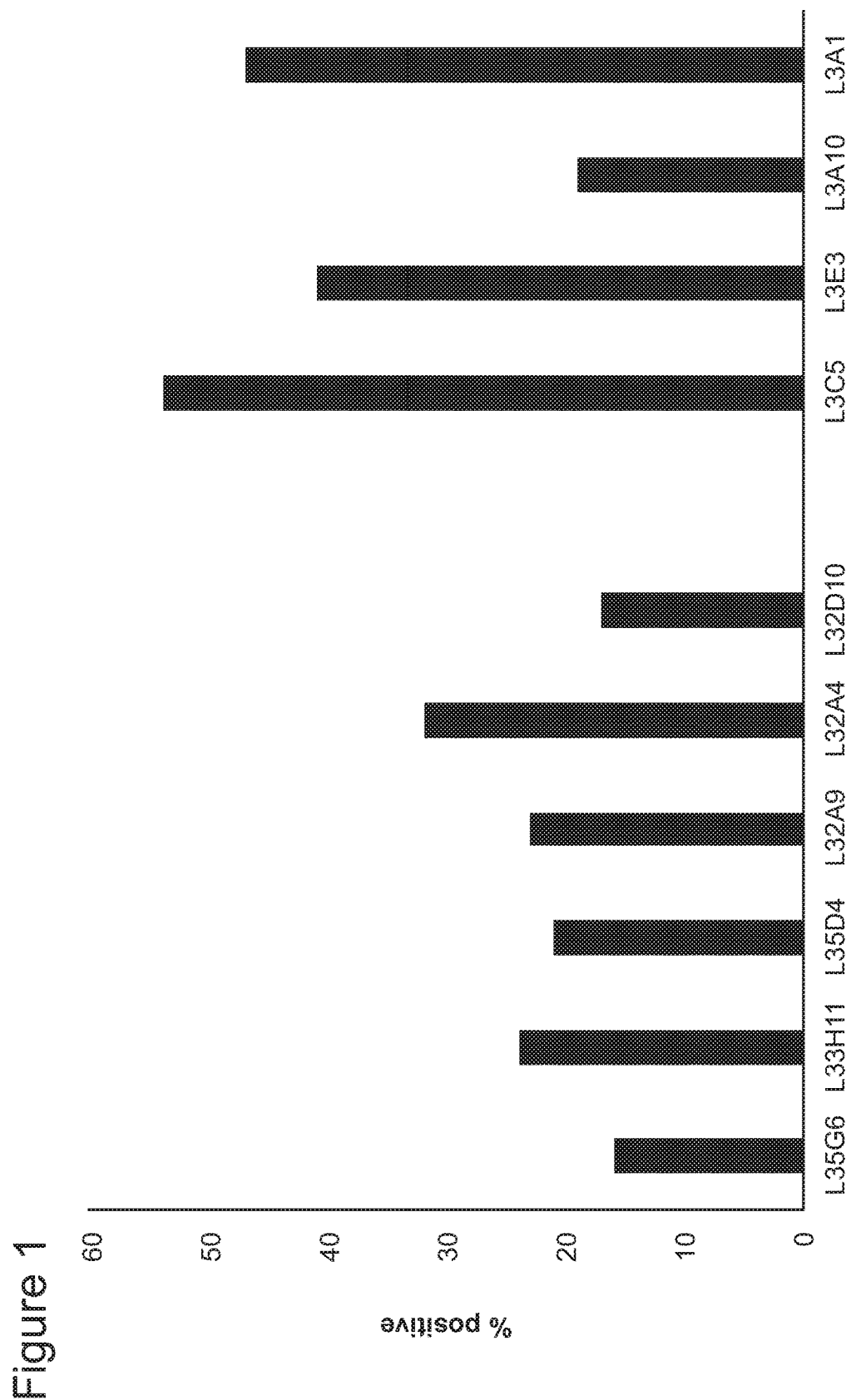
FIG. 1 is a graph that shows that several anti-LAG3 antibodies had reactivity with activated T cells, shown as % positive cells.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation.

Unless otherwise indicated, the term "antibody" includes, in addition to antibodies comprising two full-length heavy chains (each chain comprising a variable region and a constant region) and two full-length light chains (each chain comprising a variable region and a constant region), derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin, such as an IgG. An "immunoglobulin G" (or IgG) is a tetrameric molecule. In a naturally occurring IgG, each tetramer is composed of two identical pairs of polypeptide chains, each pair having one "light" (about 25 kDa) and one "heavy" chain (about 50-70 kDa). The amino-terminal portion of each chain includes a variable region (or domain) of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-LAG3 antibodies disclosed herein are characterized by their variable domain sequences in the heavy VH and light VL amino acid sequences. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain can be in accordance with the definitions of Kabat et al. in Sequences of Proteins of Immunological Interest, 5th Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, Dev. Comp. Immunol. 29:185-203; 2005) and AHo (Honegger and Pluckthun, J. Mol. Biol. 309(3):657-670; 2001).

In one embodiment, an "antibody" refers to an intact immunoglobulin, such as an IgG, or to an antigen binding portion thereof that competes with the intact antibody for specific binding, unless otherwise specified. In one embodiment, an intact antibody is an IgG1, IgG2, IgG3 or IgG4. Heavy and light chain variable domain sequences and CDRs may be selected from those described herein in SEQ ID Nos: 1 to 14 and SEQ ID Nos: 15 to 56, respectively.

The term "monospecific", as used herein, refers to an antibody that displays an affinity for one particular epitope. Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody fragment", "antigen binding portion of an antibody" or "antigen binding fragment of an antibody" comprises a portion of an intact antibody, and preferably comprises the antibody antigen binding or variable domains. Examples of an antibody fragment include a Fab, an Fab', an F(ab')2, an Fv fragment, and a linear antibody.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$, domain, or an antigen-binding fragment of a $V_H$ or $V_L$ domain (U.S. Pat. Nos. 6,846,634; 6,696,245, US App. Pub.20/0202512; 2004/0202995; 2004/0038291; 2004/0009507; 2003/0039958, and Ward et al., *Nature* 341: 544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83).

Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An antigen binding protein, such as an antibody, may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains of the antibody are derived from human immunoglobulin sequences (referred to as "a fully human antibody"). These antibodies may be prepared in a variety of ways, examples of which are described below, including through the immunization with an antigen of interest of a mouse that is genetically modified to express antibodies derived from human heavy and/or light chain-encoding genes. In a preferred embodiment, a fully human antibody is made using recombinant methods.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-LAG3 antibody. In another embodiment, all of the CDRs are derived from a human anti-LAG3 antibody. In another embodiment, the CDRs from more than one human anti-LAG3 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-LAG3 antibody, and the CDRs from the heavy chain from a third anti-LAG3 antibody. Other combinations are possible.

Further, the framework regions may be derived from one of the same anti-LAG3 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind LAG3).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human LAG3) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding proteins specificity and affinity for the antigen. For an antibody that specifically binds to its antigen, this will include at least part of at least one of its CDR domains.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with one or more expression vectors comprising the coding sequence of the antibody, where said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof that binds LAG3, which is sufficient to effect treatment, prognosis or diagnosis of a disease associated with LAG3 dependent signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material and/or chemicals. In one embodiment, an isolated antibody is expressed by a cell from a different species, e.g., a human antibody expressed in a CHO cell, and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

A "neutralizing antibody" or an "inhibitory antibody" is an antibody that inhibits the proteolytic activation of LAG3 when an excess of the anti-LAG3 antibody reduces the amount of activation by at least about 20% using an assay such as those described herein in the Examples. In various embodiments, the antigen binding protein reduces the amount of amount of proteolytic activation of LAG3 by at least 30%, 40%, 50%, 60%, 70%, 75%, 80%, 85%, 90%, 95%, 97%, 99%, and 99.9%.

LAG3 Antigen Binding Proteins

The present invention pertains to LAG3 binding proteins, particularly anti-LAG3 antibodies, or antigen-binding portions thereof, and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human LAG3, to inhibit LAG3 activity, either in vitro or in vivo, and to prevent or treat disorders such as cancer are also encompassed by the invention.

As described in Table 3 below, included in the invention are novel human antibody heavy and light chain variable regions and CDRs that are specific to human LAG3.

In one embodiment, the invention provides an anti-LAG3 antibody, or an antigen-binding fragment thereof, that comprises a heavy chain having a variable domain comprising an amino acid sequence as set forth in any one of SEQ ID NO.

1, SEQ ID NO. 8, SEQ ID NO. 10, and SEQ ID NO. 12. In one embodiment, the invention provides an anti-LAG3 antibody, or an antigen-binding fragment thereof, that comprises a light chain having a variable domain comprising an amino acid sequence as set forth in any one of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13 and SEQ ID NO. 14. In one embodiment, the invention provides an anti-LAG3 antibody, or an antigen-binding fragment thereof, that comprises a light chain having a variable domain comprising an amino acid sequence as set forth in any one of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13 and SEQ ID NO. 14; and a heavy chain having a variable domain comprising an amino acid sequence as set forth in any one of SEQ ID NO. 1, SEQ ID NO. 8, SEQ ID NO. 10, and SEQ ID NO. 12.

In one embodiment, the present disclosure provides a fully human antibody of an IgG class that binds to a LAG3 epitope with a binding affinity of at least $10^{-6}$ M, which has a heavy chain variable domain sequence which is at least 95% identical, at least 96% identical, at least 97% identical, at least 98% identical, or at least 99% identical to the amino acid sequences selected from the group consisting of SEQ ID NO. 1, SEQ ID NO. 8, SEQ ID NO. 10, SEQ ID NO. 12, and combinations thereof, and that has a light chain variable domain sequence that is at least 95% identical, at least 96% identical, at least 97% identical, at least 98% identical, or at least 99% identical to the amino acid sequence consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof.

In one embodiment, the fully human antibody has both a heavy chain and a light chain wherein the antibody has a heavy chain/light chain variable domain sequence selected from the group consisting of SEQ ID NO. 1/SEQ ID NO. 2 (called L35D4 herein), SEQ ID NO. 1/SEQ ID NO. 3 (called L35G6 herein), SEQ ID NO. 1/SEQ ID NO. 4 (called L33H11 herein), SEQ ID NO. 1/SEQ ID NO. 5 (called L32A9 herein), SEQ ID NO. 1/SEQ ID NO. 6 (called L32D10 herein), SEQ ID NO. 1/SEQ ID NO. 7 (called L32A4 herein), SEQ ID NO. 8/SEQ ID NO. 9 (called L3A1 herein), SEQ ID NO. 10/SEQ ID NO. 11 (called L3A10 herein), SEQ ID NO. 12/SEQ ID NO. 13 (called L3C5 herein), SEQ ID NO. 8/SEQ ID NO. 14 (called L3E3 herein), and combinations thereof.

Complementarity determining regions (CDRs) are known as hypervariable regions both in the light chain and the heavy chain variable domains of an antibody. The more highly conserved portions of variable domains are called the framework (FR). Complementarity determining regions (CDRs) and framework regions (FR) of a given antibody may be identified using systems known in the art, such as those described by Kabat et al. supra; Lefranc et al., supra and/or Honegger and Pluckthun, supra. For example, the numbering system described in Kabat et al. (1991, NIH Publication 91-3242, National Technical Information Service, Springfield, Va.) is well known to those in the art. Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself.

In certain embodiments, the present invention provides an anti-LAG3 antibody comprising the CDRs of the heavy and light chain variable domains described in Table 3 (SEQ ID Nos: 1 to 14). For example, the invention provides an anti-LAG3 antibody, or antigen-binding fragment thereof, comprising a heavy chain variable region having the CDRs described in an amino acid sequence as set forth in any one of SEQ ID NO. 1, SEQ ID NO. 8, SEQ ID NO. 10 and SEQ ID NO. 12. In one embodiment, the invention provides an anti-LAG3 antibody, or antigen-binding fragment thereof, comprising a light chain variable region having the CDRs described in an amino acid sequence as set forth in any one of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13 and SEQ ID NO. 14. In one embodiment, the invention provides an anti-LAG3 antibody, or antigen-binding fragment thereof, comprising a light chain variable region having the CDRs described in an amino acid sequence as set forth in any one of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13 and SEQ ID NO. 14; and a heavy chain variable region having the CDRs described in an amino acid sequence as set forth in any one of SEQ ID NO. 1, SEQ ID NO. 8, SEQ ID NO. 10 and SEQ ID NO. 12.

In one embodiment, the present invention features an isolated anti-human LAG3 (hLAG3) antibody, or an antigen-binding fragment thereof, comprising a heavy chain variable domain comprising a heavy chain CDR set (CDR1, CDR2, and CDR3) selected from the group consisting of SEQ ID Nos: 15, 16, and 17; SEQ ID Nos: 36, 37, and 38; SEQ ID Nos: 42, 43, and 44; and SEQ ID Nos: 48, 49, and 50; and a light chain variable domain comprising a light chain CDR set (CDR1, CDR2, and CDR3) selected from the group consisting of SEQ ID Nos: 18, 19, and 20; SEQ ID Nos: 21, 22, and 23; SEQ ID Nos: 24, 25, and 26; SEQ ID Nos: 27, 28, and 29; SEQ ID Nos: 30, 31, and 32; SEQ ID Nos: 33, 34, and 35; SEQ ID Nos: 39, 40, and 41; SEQ ID Nos: 45, 46, and 47; SEQ ID Nos: 51, 52, and 53; and SEQ ID Nos: 54, 55, and 56.

In one embodiment, the antibody of the invention comprises a heavy chain CDR set/light chain CDR set selected from the group consisting of the heavy chain variable domain CDR set of SEQ ID Nos: 15, 16, and 17, and the light chain variable domain CDR set of 18, 19, and 20; the heavy chain variable domain CDR set of SEQ ID Nos: 15, 16, and 17, and the light chain variable domain CDR set of 21, 22, and 23; the heavy chain variable domain CDR set of SEQ ID Nos: 15, 16, and 17, and the light chain variable domain CDR set of 24, 25, and 26; the heavy chain variable domain CDR set of SEQ ID Nos: 15, 16, and 17, and the light chain variable domain CDR set of 27, 28, and 29; the heavy chain variable domain CDR set of SEQ ID Nos: 15, 16, and 17, and the light chain variable domain CDR set of 30, 31, and 32; the heavy chain variable domain CDR set of SEQ ID Nos: 15, 16, and 17, and the light chain variable domain CDR set of 33, 34, and 35; the heavy chain variable domain CDR set of SEQ ID Nos: 36, 37, and 38, and the light chain variable domain CDR set of 39, 40, and 41; the heavy chain variable domain CDR set of SEQ ID Nos: 42, 43, and 44, and the light chain variable domain CDR set of 45, 46, and 47; the heavy chain variable domain CDR set of SEQ ID Nos: 48, 49, and 50, and the light chain variable domain CDR set of 51, 52, and 53; and the heavy chain variable domain CDR set of SEQ ID Nos: 36, 37, and 38, and the light chain variable domain CDR set of 54, 55, and 56.

In one embodiment, the invention provides an anti-LAG3 antibody, or an antigen-binding fragment thereof, comprising a heavy chain comprising a CDR3 domain as set forth in any one of SEQ ID NO. 1, SEQ ID NO. 8, SEQ ID NO. 10 or SEQ ID NO. 12, and comprising a variable domain comprising an amino acid sequence that has at least 95%, at least 96%, at least 97%, at least 98%, or at least 99% identical to a sequence as set forth in any one of SEQ ID NO. 1, SEQ ID NO. 8, SEQ ID NO. 10 or SEQ ID NO. 12. In one embodiment, the invention provides an anti-LAG3 antibody, or an antigen-binding fragment thereof, comprising a light chain comprising a CDR3 domain as set forth in any one of SEQ ID NO.2, SEQ ID NO.3, SEQ ID NO.4, SEQ ID NO.5, SEQ ID NO.6, SEQ ID NO. 7, SEQ ID NO. 9, SEQ ID NO.11, SEQ ID NO.13 or SEQ ID NO.14, and having a light chain variable domain comprising an amino acid sequence that has at least 95%, at least 96%, at least 97%, at least 98%, or at least 99% identical to a sequence as set forth in any one of SEQ ID NO.2, SEQ ID NO.3, SEQ ID NO.4, SEQ ID NO.5, SEQ ID NO.6, SEQ ID NO. 7, SEQ ID NO. 9, SEQ ID NO.11, SEQ ID NO.13 and SEQ ID NO.14. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to LAG3 and retains the functional characteristics, e.g., binding affinity, of the parent.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 3.

In one embodiment, the present invention is directed to an antibody, or an antigen binding fragment thereof, having antigen binding regions of antibody L35D4. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 2. In one embodiment, the invention is directed to an antibody having a heavy chain variable domain comprising the CDRs of SEQ ID NO: 1, and a light chain variable domain comprising the CDRs of SEQ ID NO: 2. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 2. In one embodiment, the invention features an anti-LAG3 antibody, or an antigen-binding portion thereof, comprising a heavy chain variable region comprising a CDR3 domain comprising the amino acid as set forth in SEQ ID NO: 17, a CDR2 domain comprising the amino acid sequence as set forth in SEQ ID NO: 16, and a CDR1 domain comprising the amino acid sequence as set forth in SEQ ID NO: 15; and comprising a light chain variable region comprising a CDR3 domain comprising the amino acid as set forth in SEQ ID NO: 20, a CDR2 domain comprising the amino acid sequence as set forth in SEQ ID NO: 19, and a CDR1 domain comprising the amino acid sequence as set forth in SEQ ID NO: 18. The antibody may further be an IgG1 or an IgG4 isotype.

In one embodiment, the present invention is directed to an antibody, or an antigen binding fragment thereof, having antigen binding regions of antibody L35G6. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 3. In one embodiment, the invention is directed to an antibody having a heavy chain variable domain comprising the CDRs of SEQ ID NO: 1, and a light chain variable domain comprising the CDRs of SEQ ID NO:3. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 3. In one embodiment, the invention features an anti-LAG3 antibody, or an antigen-binding portion thereof, comprising a heavy chain variable region comprising a CDR3 domain comprising the amino acid as set forth in SEQ ID NO: 17, a CDR2 domain comprising the amino acid sequence as set forth in SEQ ID NO: 16, and a CDR1 domain comprising the amino acid sequence as set forth in SEQ ID NO: 15; and comprising a light chain variable region comprising a CDR3 domain comprising the amino acid as set forth in SEQ ID NO: 23, a CDR2 domain comprising the amino acid sequence as set forth in SEQ ID NO: 22, and a CDR1 domain comprising the amino acid sequence as set forth in SEQ ID NO: 21. The antibody may further be an IgG1 or an IgG4 isotype.

In one embodiment, the present invention is directed to an antibody, or an antigen binding fragment thereof, having antigen binding regions of antibody L33H11. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 4. In one embodiment, the invention is directed to an antibody having a heavy chain variable domain comprising the CDRs of SEQ ID NO: 1, and a light chain variable domain comprising the CDRs of SEQ ID NO: 4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 4. In one embodiment, the invention features an anti-LAG3 antibody, or an antigen-binding portion thereof, comprising a heavy chain variable region comprising a CDR3 domain comprising the amino acid as set forth in SEQ ID NO: 17, a CDR2 domain comprising the amino acid sequence as set forth in SEQ ID NO: 16, and a CDR1 domain comprising the amino acid sequence as set forth in SEQ ID NO: 15; and comprising a light chain variable region comprising a CDR3 domain comprising the amino acid as set forth in SEQ ID NO: 26, a CDR2 domain comprising the amino acid sequence as set forth in SEQ ID NO: 25, and a CDR1 domain comprising the amino acid sequence as set forth in SEQ ID NO: 24. The antibody may further be an IgG1 or an IgG4 isotype.

In one embodiment, the present invention is directed to an antibody, or an antigen binding fragment thereof, having antigen binding regions of antibody L32A9. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 5. In one embodiment, the invention is directed to an antibody having a heavy chain variable domain comprising the CDRs of SEQ ID NO: 1, and a light chain variable domain comprising the CDRs of SEQ ID NO: 5. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 5. In one embodiment, the invention features an anti-LAG3 antibody, or an antigen-binding portion thereof, comprising a heavy chain variable region comprising a CDR3 domain comprising the amino acid as set forth in SEQ ID NO: 17, a CDR2 domain comprising the amino acid sequence as set forth in SEQ ID NO: 16, and a CDR1 domain comprising the amino acid sequence as set forth in SEQ ID NO: 15; and comprising a light chain variable region comprising a CDR3 domain comprising the amino acid as set forth in SEQ ID NO: 29, a CDR2 domain comprising the amino acid sequence as set forth in SEQ ID NO: 28, and a CDR1 domain comprising the amino acid sequence as set forth in SEQ ID NO: 27. The antibody may further be an IgG1 or an IgG4 isotype.

In one embodiment, the present invention is directed to an antibody, or an antigen binding fragment thereof, having antigen binding regions of antibody L32D10. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 6. In one embodiment, the invention is directed to an antibody having a heavy chain variable domain comprising the CDRs of SEQ ID NO: 1, and a light chain variable domain comprising the CDRs of SEQ ID NO: 6. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 6. In one embodiment, the invention features an anti-LAG3 antibody, or an antigen-binding portion thereof, comprising a heavy chain variable region comprising a CDR3 domain comprising the amino acid as set forth in SEQ ID NO: 17, a CDR2 domain comprising the amino acid sequence as set forth in SEQ ID NO: 16, and a CDR1 domain comprising the amino acid sequence as set forth in SEQ ID NO: 15; and comprising a light chain variable region comprising a CDR3 domain comprising the amino acid as set forth in SEQ ID NO: 32, a CDR2 domain comprising the amino acid sequence as set forth in SEQ ID NO: 31, and a CDR1 domain comprising the amino acid sequence as set forth in SEQ ID NO: 30. The antibody may further be an IgG1 or an IgG4 isotype.

In one embodiment, the present invention is directed to an antibody, or an antigen binding fragment thereof, having antigen binding regions of antibody L32A4. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 7. In one embodiment, the invention is directed to an antibody having a heavy chain variable domain comprising the CDRs of SEQ ID NO: 1, and a light chain variable domain comprising the CDRs of SEQ ID NO: 7. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 7. In one embodiment, the invention features an anti-LAG3 antibody, or an antigen-binding portion thereof, comprising a heavy chain variable region comprising a CDR3 domain comprising the amino acid as set forth in SEQ ID NO: 17, a CDR2 domain comprising the amino acid sequence as set forth in SEQ ID NO: 16, and a CDR1 domain comprising the amino acid sequence as set forth in SEQ ID NO: 15; and comprising a light chain variable region comprising a CDR3 domain comprising the amino acid as set forth in SEQ ID NO: 35, a CDR2 domain comprising the amino acid sequence as set forth in SEQ ID NO: 34, and a CDR1 domain comprising the amino acid sequence as set forth in SEQ ID NO: 33. The antibody may further be an IgG1 or an IgG4 isotype.

In one embodiment, the present invention is directed to an antibody, or an antigen binding fragment thereof, having antigen binding regions of antibody L3A1. In one embodiment, the invention provides an antibody, or antigen-binding fragment thereof, comprising a heavy chain variable domain sequence as set forth in SEQ ID NO: 8, and a light chain variable domain sequence as set forth in SEQ ID NO: 9. In one embodiment, the invention is directed to an antibody having a heavy chain variable domain comprising the CDRs of SEQ ID NO: 8, and a light chain variable domain comprising the CDRs of SEQ ID NO: 9. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 8, and comprises a light chain variable region having an amino acid sequence that is at least 95% identical, at least 96% identical, at least 97% identical, at least 98% identical, or at least 99% identical to the sequence set forth in SEQ ID NO: 9. In one embodiment, the invention features an anti-LAG3 antibody, or an antigen-binding portion thereof, comprising a heavy chain variable region comprising a CDR3 domain comprising the amino acid as set forth in SEQ ID NO: 38, a CDR2 domain comprising the amino acid sequence as set forth in SEQ ID NO: 37, and a CDR1 domain comprising the amino acid sequence as set forth in SEQ ID NO: 36; and comprising a light chain variable region comprising a CDR3 domain comprising the amino acid as set forth in SEQ ID NO: 41, a CDR2 domain comprising the amino acid sequence as set forth in SEQ ID NO: 40, and a CDR1 domain comprising the amino acid sequence as set forth in SEQ ID NO: 39. The antibody may further be an IgG1 or an IgG4 isotype.

In one embodiment, the present invention is directed to an antibody, or an antigen binding fragment thereof, having antigen binding regions of antibody L3A10. In one embodiment, the invention provides an antibody, or antigen-binding fragment thereof, comprising a heavy chain variable domain sequence as set forth in SEQ ID NO: 10, and a light chain variable domain sequence as set forth in SEQ ID NO: 11. In one embodiment, the invention is directed to an antibody having a heavy chain variable domain comprising the CDRs of SEQ ID NO: 10, and a light chain variable domain comprising the CDRs of SEQ ID NO: 11. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 10, and comprises a light chain variable region having an amino acid sequence that is at least 95% identical, at least 96% identical, at least 97% identical, at least 98% identical, or at least 99% identical to the sequence set forth in SEQ ID NO: 11. In one embodiment, the invention features an anti-LAG3 antibody, or an antigen-binding portion thereof, comprising a heavy chain variable region comprising a CDR3 domain comprising the amino acid as set forth in SEQ ID NO: 44, a CDR2 domain comprising the amino acid sequence as set forth in SEQ ID NO: 43, and a CDR1 domain comprising the amino acid sequence as set forth in SEQ ID NO: 42; and comprising a light chain variable region comprising a CDR3 domain comprising the amino acid as set forth in SEQ ID NO: 47, a CDR2 domain comprising the amino acid sequence as set forth in SEQ ID NO: 46, and a CDR1 domain comprising the amino acid sequence as set forth in SEQ ID NO: 45. The antibody may further be an IgG1 or an IgG4 isotype.

In one embodiment, the present invention is directed to an antibody, or an antigen binding fragment thereof, having antigen binding regions of antibody L3C5. In one embodiment, the invention provides an antibody, or antigen-binding fragment thereof, comprising a heavy chain variable domain sequence as set forth in SEQ ID NO: 12, and a light chain variable domain sequence as set forth in SEQ ID NO: 13. In one embodiment, the invention is directed to an antibody having a heavy chain variable domain comprising the CDRs of SEQ ID NO: 12, and a light chain variable domain comprising the CDRs of SEQ ID NO: 13. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 12, and comprises a light chain variable region having an amino acid sequence that is at least 95% identical, at least 96% identical, at least 97% identical, at least 98% identical, or at least 99% identical to the sequence set forth in SEQ ID NO: 13. In one embodiment, the invention features an anti-LAG3 antibody, or an antigen-binding portion thereof, comprising a heavy chain variable region comprising a CDR3 domain comprising the amino acid as set forth in SEQ ID NO: 50, a CDR2 domain comprising the amino acid sequence as set forth in SEQ ID NO: 49, and a CDR1 domain comprising the amino acid sequence as set forth in SEQ ID NO: 48; and comprising a light chain variable region comprising a CDR3 domain comprising the amino acid as set forth in SEQ ID NO: 53, a CDR2 domain comprising the amino acid sequence as set forth in SEQ ID NO: 52, and a CDR1 domain comprising the amino acid sequence as set forth in SEQ ID NO: 51. The antibody may further be an IgG1 or an IgG4 isotype.

In one embodiment, the present invention is directed to an antibody, or an antigen binding fragment thereof, having antigen binding regions of antibody L3E3. In one embodiment, the invention provides an antibody, or antigen-binding fragment thereof, comprising a heavy chain variable domain sequence as set forth in SEQ ID NO: 8, and a light chain variable domain sequence as set forth in SEQ ID NO: 14. In one embodiment, the invention is directed to an antibody having a heavy chain variable domain comprising the CDRs of SEQ ID NO: 8, and a light chain variable domain comprising the CDRs of SEQ ID NO: 14. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 8, and comprises a light chain variable region having an amino acid sequence that is at least 95% identical, at least 96% identical, at least 97% identical, at least 98% identical, or at least 99% identical to the sequence set forth in SEQ ID NO. 14. In one embodiment, the invention features an anti-LAG3 antibody, or an antigen-binding portion thereof, comprising a heavy chain variable region comprising a CDR3 domain comprising the amino acid as set forth in SEQ ID NO: 38, a CDR2 domain comprising the amino acid sequence as set forth in SEQ ID NO: 37, and a CDR1 domain comprising the amino acid sequence as set forth in SEQ ID NO: 36; and comprising a light chain variable region comprising a CDR3 domain comprising the amino acid as set forth in SEQ ID NO: 56, a CDR2 domain comprising the amino acid sequence as set forth in SEQ ID NO: 55, and a CDR1 domain comprising the amino acid sequence as set forth in SEQ ID NO: 54. The antibody may further be an IgG1 or an IgG4 isotype.

As described in Table 3, antibodies L35D4, L35G6, L33H11, L32A9, L32D10 and L32A4, have a heavy chain variable region having an amino acid sequence as set forth in SEQ ID NO.1. As also described in Table 3, SEQ ID NO.1 is at least 95% identical to SEQ ID NO:8 (as described for L3A1 and L3E3).

As described in Table 3, SEQ ID NO: 7 (as described for L32A4) is at least 95% identical to SEQ ID NO.9 (as described for L3A1).

Antigen-binding fragments of antigen binding proteins of the invention may be produced by conventional techniques. Examples of such fragments include, but are not limited to, Fab and F(ab')2 fragments.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different VL and VH-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

In certain embodiments, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, at least 99%, or 100% identical, to the amino acid sequences selected from the group consisting of SEQ ID NO. 1, SEQ ID NO. 8, SEQ ID NO. 10, SEQ ID NO. 12, and combinations thereof, and that has a light chain variable domain sequence that is at least 95% identical, at least 96% identical, at least 97% identical, at least 98% identical, at least 99%, or 100% identical to the amino acid sequence consisting of SEQ ID NO. 2, SEQ ID NO. 3, SEQ ID NO. 4, SEQ ID NO. 5, SEQ ID NO. 6, SEQ ID NO. 7, SEQ ID NO: 9, SEQ ID NO. 11, SEQ ID NO. 13, SEQ ID NO. 14, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, SEQ ID NO. 8/SEQ ID NO. 14, and combinations thereof.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, at least 99% identical, or 100% identical to the amino acid sequences selected from the group consisting of SEQ ID NO. 1, SEQ ID NO. 8, SEQ ID NO. 10, SEQ ID NO. 12, and that has a light chain variable domain sequence that is at least 95% identical, at least 96% identical, at least 97% identical, at least 98% identical, at least 99%, or 100% identical to the amino acid sequence consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, SEQ ID NO. 8/SEQ ID NO. 14, and combinations thereof.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)). Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

In certain embodiments, an antibody, or antigen-binding fragment thereof, of the invention has a dissociation constant ($K_D$) of $1\times10^{-6}$ M or less; $5\times10^{-7}$ M or less' $1\times10^{-7}$ M or less; $5\times10^{-8}$ M or less; $1\times10^{-8}$ M or less; $5\times10^{-9}$ M or less; or $1\times10^{-9}$ M or less. In one embodiment, the antibody, or antigen-binding fragment thereof, of the invention as a $K_D$ from $1\times10^{-7}$ M to $1\times10^{-10}$ M. In one embodiment, the antibody, or antigen-binding fragment thereof, of the invention as a $K_D$ from $1\times10^{-8}$ M to $1\times10^{-10}$ M.

Those of ordinary skill in the art will appreciate standard methods known for determining the $K_D$ of an antibody, or fragment thereof. For example, in one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)).

According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.). Surface plasmon resonance can also be used to determine $K_{off}$ and $K_a$ values.

In particular embodiments, antigen binding proteins of the present invention have a binding affinity ($K_a$) for LAG3 of at least $10^3$ $M^{-1}S^{-1}$. In other embodiments, the antigen binding proteins exhibit a $K_a$ of at least $10^3$ $M^{-1}S^{-1}$, at least $10^4$ $M^{-1}S^{-1}$, at least $10^5$ $M^{-1}S^{-1}$, or at least $10^6$ $M^{-1}S^{-1}$. In other further embodiments, the antigen binding proteins exhibit a $K_a$ of at least $10^7$ $M^{-1}S^{-1}$. In other further embodiments, the antigen binding proteins exhibit a $K_a$ of at least $10^7$ $M^{-1}S^{-1}$, at least $10^8$ $M^{-1}S^{-1}$, at least $10^9M^{-1}S^{-1}$, or at least $10^{10}$ $M^{-1}S^{-1}$. In one embodiment, the anti-LAG3 antibody, or fragment thereof, of the invention has a $K_a$ of at least $10^3$-$10^7$ $M^{-1}S^{-1}$. In another embodiment, the antigen binding protein exhibits a $K_a$ substantially the same as that of an antibody described herein in the Examples. $K_a$ can be determined by Biacore testing, for example with Biacore 3000 or T200.

In another embodiment, the present disclosure provides an antigen binding protein that has a low dissociation rate from LAG3. In one embodiment, the antigen binding protein has a $K_{off}$ of $1\times10^{-4}$ to $10^{-1}$ $sec^{-1}$ or lower. In another embodiment, the $K_{off}$ is $5\times10^{-5}$ to $10^{-1}$ $sec^{-1}$ sec or lower. In another embodiment, the $K_{off}$ is $5\times10^{-6}$ to $10^{-1}$ $sec^{-1}$ or lower. In another embodiment, the $K_{off}$ is substantially the same as an antibody described herein. In another embodiment, the antigen binding protein binds to LAG3 with substantially the same $K_{off}$ as an antibody described herein.

In another aspect, the present disclosure provides an antigen binding protein that inhibits an activity of LAG3. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of LAG3 with substantially the same $IC_{50}$ as an antibody described herein.

In another aspect, the present disclosure provides an antigen binding protein that binds to LAG3 expressed on the surface of a cell and, when so bound, inhibits LAG3 signaling activity in the cell without causing a significant reduction in the amount of LAG3 on the surface of the cell. Any method for determining or estimating the amount of LAG3 on the surface and/or in the interior of the cell can be used. In other embodiments, binding of the antigen binding protein to the LAG3-expressing cell causes less than about 75%, 50%, 40%, 30%, 20%, 15%, 10%, 5%, 1%, or 0.1% of the cell-surface LAG3 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of LAG3, or to an epitope of LAG3 and an epitope of another molecule, via two different antigen binding sites or regions. Moreover, bispecific antigen binding protein as disclosed herein can comprise a LAG3 binding site from one of the herein-described antibodies and a second LAG3 binding region from another of the herein-described antibodies, including those described herein by reference to other publications. Alternatively, a bispecific antigen binding protein may comprise an antigen binding site from one of the herein described antibodies and a second antigen binding site from another LAG3 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, Nature 305:537, and chemical coupling of antibody fragments (Brennan et al., 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Oligomers that contain one or more antigen binding proteins may be employed as LAG3 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have LAG3 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a LAG3 binding fragment of an anti-LAG3 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-LAG3 antibody fragment or derivative fused to a leucine zipper peptide are expressed in suitable host cells, and the soluble oligomeric anti-LAG3 antibody fragments or derivatives that form are recovered from the culture supernatant.

Antigen binding proteins directed against LAG3 can be used, for example, in assays to detect the presence of LAG3 polypeptides, either in vitro or in vivo. The antigen binding proteins also may be employed in purifying LAG3 proteins by immunoaffinity chromatography. Blocking antigen binding proteins can be used in the methods disclosed herein. Such antigen binding proteins that function as LAG3 antagonists may be employed in treating any LAG3-induced condition, including but not limited to various cancers.

Antigen binding proteins may be employed in an in vitro procedure, or administered in vivo to inhibit LAG3-induced biological activity. Disorders caused or exacerbated (directly or indirectly) by the proteolytic of LAG3, examples of which are provided herein, thus may be treated. In one embodiment, the present invention provides a therapeutic method comprising in vivo administration of a LAG3 blocking antigen binding protein to a mammal in need thereof in an amount effective for reducing a LAG3-induced biological activity.

In certain embodiments of the invention, antigen binding proteins include fully human monoclonal antibodies that inhibit a biological activity of LAG3.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or *bacilli*. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of LAG3 bound thereto. Polypeptides contemplated for use herein include substantially homogeneous recombinant mammalian anti-LAG3 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-LAG3 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (a cDNA) encoding the polypeptide into a recombinant expression vector and expressing the DNA sequence under conditions promoting expression. The invention includes nucleic acids encoding any of the polypeptide sequences described in SEQ ID Nos: 1 to 56, as well as vectors comprising said nucleic acid sequences.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

LAG3-binding polypeptides can also be produced by chemical synthesis (such as by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to LAG3. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen-binding fragments of antigen binding proteins of the invention may be produced by conventional techniques.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 1123-161). The term "PEG" is used broadly to encompass any polyethylene glycol molecule, without regard to size or to modification at an end of the PEG, and can be represented by the formula: X—O(CH$_2$CH$_2$O)$_n$—CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half-life, such as the half-life of the protein in the serum or other bodily fluid of an animal.

Therapeutic Methods, Formulations and Modes of Administration

The present disclosure further provides a method for treating a broad spectrum of mammalian cancers, infectious diseases, or autoimmune reactions, In one embodiment, the present disclosure features methods for treating or preventing the *S. aureus* infection comprising administering anti-LAG3 antibodies or antigen binding fragments of the present invention.

The present disclosure further provides a method for treating a broad spectrum of mammalian cancers, infectious diseases, or autoimmune reactions, comprising administering an anti-LAG3 polypeptide using the antibodies, and antibody fragments, disclosed herein. In one embodiment, the invention provides a method of treating cancer by administering an anti-human LAG3 antibody to a subject in need thereof. Examples of antibodies, and fragments thereof, that may be used in the therapeutics methods disclosed herein include an anti-human LAG3 human antibody of an IgG class having a binding affinity of at least 10$^{-6}$ M, or an anti-human LAG3 Fab antibody fragment comprising a heavy chain variable region and a light chain variable region from the antibody sequences described in SEQ ID Nos. 1-14 or comprising the CDRs described in any of the antibody sequences of SEQ ID Nos: 1-14. In one embodiment, the methods disclosed herein comprise administering a fully human antibody comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 8, SEQ ID NO. 10, SEQ ID NO. 12, and combinations thereof, and having a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof. In one embodiment, the methods disclosed herein comprise administering an IgG human anti-hLAG3 antibody comprising a heavy chain variable domain sequence selected from the group consisting of SEQ ID NO. 1, SEQ ID NO. 8, SEQ ID NO. 10, SEQ ID NO. 12, and having a light chain variable domain sequence selected form the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14.

In one embodiment, the methods described herein include the use of a fully human Fab antibody fragment comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 8, SEQ ID NO. 10, SEQ ID NO. 12, and combinations thereof, and comprising a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof. In one embodiment, the methods described herein include the use of a human Fab antibody fragment comprising a heavy chain variable domain sequence selected from the group consisting of SEQ ID NO. 1, SEQ ID NO. 8, SEQ ID NO. 10, SEQ ID NO. 12, and comprising a light chain variable domain sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14.

In one embodiment, the methods described herein include the use of a single chain human antibody comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 8, SEQ ID NO. 10, SEQ ID NO. 12, and combinations thereof, and comprising a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14, and combinations thereof. In one embodiment, the methods described herein include the use of a single chain human antibody comprising a heavy chain variable domain having an amino acid sequence selected from the group consisting of SEQ ID NO. 1, SEQ ID NO. 8, SEQ ID NO. 10, SEQ ID NO. 12, and comprising a light chain variable domain having an amino acid sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 9, SEQ ID NO. 11, SEQ ID NO. 13, SEQ ID NO. 14

In one embodiment, the fully human antibody has both a heavy chain and a light chain wherein the antibody has a heavy chain/light chain variable domain sequence selected from the group consisting of SEQ ID NO. 1/SEQ ID NO. 2 (called L35D4 herein), SEQ ID NO. 1/SEQ ID NO. 3 (called L35G6 herein), SEQ ID NO. 1/SEQ ID NO. 4 (called L33H11 herein), SEQ ID NO. 1/SEQ ID NO. 5 (called L32A9 herein), SEQ ID NO. 1/SEQ ID NO. 6 (called L32D10 herein), SEQ ID NO. 1/SEQ ID NO. 7 (called L32A4 herein), SEQ ID NO. 8/SEQ ID NO. 9 (called L3A1 herein), SEQ ID NO. 10/SEQ ID NO. 11 (called L3A10 herein), SEQ ID NO. 12/SEQ ID NO. 13 (called L3C5 herein), SEQ ID NO. 8/SEQ ID NO. 14 (called L3E3 herein), and combinations thereof.

In one embodiment, a fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called L35D4 herein), SEQ ID NO. 1/SEQ ID NO. 3 (called L35G6 herein), SEQ ID NO. 1/SEQ ID NO. 4 (called L33H11 herein), SEQ ID NO. 1/SEQ ID NO. 5 (called L32A9 herein), SEQ ID NO. 1/SEQ ID NO. 6 (called L32D10 herein), SEQ ID NO. 1/SEQ ID NO. 7 (called L32A4 herein), SEQ ID NO. 8/SEQ ID NO. 9 (called L3A1 herein), SEQ ID NO. 10/SEQ ID NO. 11 (called L3A10 herein), SEQ ID NO. 12/SEQ ID NO. 13 (called L3C5 herein), SEQ ID NO. 8/SEQ ID NO. 14 (called L3E3 herein).

In one embodiment, a fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 1/SEQ ID NO. 3, SEQ ID NO. 1/SEQ ID NO. 4, SEQ ID NO. 1/SEQ ID NO. 5, SEQ ID NO. 1/SEQ ID NO. 6, SEQ ID NO. 1/SEQ ID NO. 7, SEQ ID NO. 8/SEQ ID NO. 9, SEQ ID NO. 10/SEQ ID NO. 11, SEQ ID NO. 12/SEQ ID NO. 13, SEQ ID NO. 8/SEQ ID NO. 14.

Cancer Indications

Anti-LAG3 antibodies and antibody fragments of the invention may be used to treat cancer. Examples of cancer that may be treated include, but are not limited to, glioblastoma, non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

In one embodiment, the LAG3 antibodies and antibody fragments described herein are useful in treating, delaying the progression of, preventing relapse of or alleviating a symptom of a cancer or other neoplastic condition, including, hematological malignancies and/or LAG3+ tumors. The LAG3 antibodies and antibody fragments described herein are useful in treating a cancer selected from the group consisting of non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, glioblastoma, and solid tumors, wherein solid tumors are selected from the group consisting of breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

As used herein, "hematological cancer" refers to a cancer of the blood, and includes leukemia, lymphoma and myeloma among others. "Leukemia" refers to a cancer of the blood in which too many white blood cells that are ineffective in fighting infection are made, thus crowding out the other parts that make up the blood, such as platelets and red blood cells. Cases of leukemia are classified as acute or chronic.

Certain forms of leukemia include, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma.

Blockade of LAG3 by antibodies can enhance an immune response against cancerous cells in the patient. An anti-LAG3 antibody or antibody fragment disclosed herein can be used alone to inhibit the growth of cancerous tumors. Alternatively, an anti-LAG3 antibody or antibody fragment disclosed herein can be used in conjunction with other immunogenic agents, standard cancer treatments, or other antibodies. In one embodiment, the present disclosure provides a method of inhibiting growth of tumor cells in a subject, comprising administering to the subject a therapeutically effective amount of an anti-LAG3 antibody, or antigen-binding fragment thereof. Preferably, the antibody or antibody fragment is a human anti-LAG-3 antibody or antibody fragment (such as any of the human anti-LAG3 antibodies described herein).

In one embodiment, preferred cancers whose growth may be inhibited include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer, fibrosarcoma, and lung cancer (e.g. non-small cell lung cancer). Examples of other cancers that can be treated using the disclosed antibodies include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Other cancers that can be treated with the disclosed antibodies are metastatic cancers, especially metastatic cancers that express PD-L1 (Iwai et al. (2005) *Int. Immunol.* 17:133-144).

Optionally antibodies and antibody fragments to LAG3 described herein can be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. By raising the threshold of T cell activation by LAG3 blockade, the tumor responses in the host can be activated.

LAG3 blockade is likely to be more effective when combined with a vaccination protocol. Many experimental strategies for vaccination against tumors have been devised. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. LAG3 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with LAG3 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with LAG3 blockade to activate more potent anti-tumor responses.

LAG3 blockade (using the anti-LAG3 antibodies and fragments disclosed herein) can also be combined with standard cancer treatments. LAG3 blockade can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-LAG3 antibody in combination with decarbazine for the treatment of melanoma. Another example of such a combination is an anti-LAG3 antibody in combination with interleukin-2 (IL-2) for the treatment of melanoma. The scientific rationale behind the combined use of LAG3 blockade and chemotherapy is that cell death, that is a consequence of the cytotoxic action of most chemotherapeutic compounds, should result in increased levels of tumor antigen in the antigen presentation pathway. Other combination therapies that may result in synergy with LAG3 blockade through cell death are radiation, surgery, and hormone deprivation. Each of these protocols creates a source of tumor antigen in the host. Angiogenesis inhibitors can also be combined with LAG3 blockade Inhibition of angiogenesis often leads to tumor cell death which may feed tumor antigens into host antigen presentation pathways.

Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of LAG3 blockade using anti-LAG3 antibodies and antibody fragments described herein. Alternatively, antigen may be delivered directly to DCs by the use of bispecific antibodies which bind to tumor antigen and a dendritic cell specific cell surface marker.

Bispecific antibodies can be used to target two separate tumor antigens. A variety of tumor targets may be considered, including, for example, Her2, cMet, EGFR and VEGFR expressing tumors. As such, in one embodiment, the invention provides a bispecific antibody comprising an anti-LAG3 antibody (or antigen binding fragment) comprising a heavy and light chain variable region sequence as described herein or a heavy and light chain variable region comprising a set of CDR sequences as described herein and an anti-Her2, an anti-EGFR, an anti-VEGFR (see, for examples, antibodies described in U.S. Pat. No. 9,029,510, incorporated by reference herein), or an anti-cMet antibody (or antigen binding portion thereof). In one embodiment, the invention includes a bispecific antibody specific to LAG3 and EGFR, wherein the antibody comprises an anti-LAG3 antibody or fragment as disclosed herein and an anti-EGFR antibody or fragment as described in International Publication No. WO 2013/173255 or International Publication No. WO 2014/066530, both of which are incorporated by reference in their entireties herein. In one embodiment, the invention includes a bispecific antibody specific to LAG3 and VEGFR, wherein the antibody comprises an anti-LAG3 antibody or fragment as disclosed herein and an anti-VEGFR antibody or fragment as described in U.S. Pat. No. 9,029,510, incorporated by reference in its entirety herein. In one embodiment, the invention includes a bispecific antibody specific to LAG3 and cMet, wherein the antibody comprises an anti-LAG3 antibody or fragment as disclosed herein and an anti-cMet antibody or fragment as described in International Publication No. WO 2016/094455, incorporated by reference in its entirety herein.

LAG3 blocking antibodies and antibody fragments described herein can also be used in combination with bispecific antibodies that target, for example, Fcα or Fcγ receptor-expressing effectors cells to tumor cells (U.S. Pat. Nos. 5,922,845 and 5,837,243).

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-LAG3 antibodies and antibody fragments described herein to counteract the effects of the immunosuppressive agent and favor tumor immune responses by the host.

Other antibodies which activate host immune responsiveness can be used in combination with anti-LAG3 antibodies and antibody fragments described herein. These include molecules on the surface of dendritic cells which activate DC function and antigen presentation. Anti-CD40 antibodies are able to substitute effectively for T cell helper activity (Ridge et al. (1998) Nature 393: 474-478) and can be used in conjunction with LAG3 antibodies (Ito et al. (2000) *Immunobiology* 201 (5) 527-40). Activating antibodies to T cell costimulatory molecules such as CTLA-4, OX-40, 4-1BB, and ICOS may also provide for increased levels of T cell activation. LAG3 blockade can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-LAG3 antibodies can increase the frequency and activity of the adoptively transferred T cells.

Additional methods for treating cancer using the anti-LAG3 antibodies and fragments of the invention are disclosed below, for example, in the Combination Therapy section.

Infectious Diseases

The present disclosure further provides a method of treating an infectious disease in a subject comprising administering to the subject an anti-LAG3 antibody, or antigen-binding portion thereof, such that the subject is treated for the infectious disease. Preferably, the antibody is a human anti-human LAG3 antibody or antibody fragment (such as any of the human anti-LAG-3 antibodies described herein) Similar to its application to tumors, antibody mediated LAG3 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, *Giardia*, Malaria, *Leishmania, Staphylococcus aureus, Pseudomonas aeruginosa*. LAG3 blockade is particularly useful against established infections by agents such as HIV that present altered antigens over the course of the infections. These novel epitopes are recognized as foreign at the time of anti-human LAG3 administration, thus provoking a strong T cell response that is not dampened by negative signals through LAG3.

Some examples of pathogenic viruses causing infections treatable by the disclosed antibodies include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by the disclosed antibodies include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by the disclosed antibodies include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by the disclosed antibodies include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

LAG3 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Autoimmune Reactions

Anti-LAG3 antibodies may provoke and amplify autoimmune responses. Indeed, induction of anti-tumor responses using tumor cell and peptide vaccines reveals that many anti-tumor responses involve anti-self reactivities (van Elsas et al. (2001) *J. Exp. Med.* 194:481-489; Overwijk, et al. (1999) *Proc. Natl. Acad. Sci. U.S.A.* 96: 2982-2987; Hurwitz, (2000) supra; Rosenberg & White (1996) *J. Immunother Emphasis Tumor Immunol* 19 (1): 81-4). Therefore, it is possible to consider using anti-LAG3 antibodies like those described herein in a LAG3 blockade in conjunction with various self proteins in order to devise vaccination protocols to efficiently generate immune responses against these self proteins for disease treatment. For example, Alzheimer's disease involves inappropriate accumulation of Aβ peptide in amyloid deposits in the brain; antibody responses against amyloid are able to clear these amyloid deposits (Schenk et al., (1999) *Nature* 400: 173-177).

Other self proteins can also be used as targets such as IgE for the treatment of allergy and asthma, and TNFα for rheumatoid arthritis. Finally, antibody responses to various hormones may be induced by the use of anti-LAG-3 antibody. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-LAG3 antibodies and antibody fragments can be used for induction of therapeutic autoimmune responses to treat patients having an inappropriate accumulation of other self-antigens, such as amyloid deposits, including Aβ in Alzheimer's disease, cytokines such as TNFα, and IgE. Further, anti-LAG3 antibodies and antibody fragments can be used for induction of therapeutic autoimmune responses to treat patients having other autoimmune diseases, including but not limited to, celiac disease, Crohn's disease, Grave's disease, inflammatory bowel disease (IBD), lupus, multiple sclerosis, Myasthenia Gravis, polymyalgia rheumatic, rheumatoid arthritis, type I diabetes, and vasculitis.

Vaccines

The anti-LAG3 antibodies and antibody fragments of the invention can be used to stimulate antigen-specific immune responses by coadministration of an anti-LAG3 antibody or antibody portion with an antigen of interest (e.g., a vaccine). Accordingly, this disclosure further provides a method of enhancing an immune response to an antigen in a subject, comprising administering to the subject: (i) the antigen; and (ii) an anti-LAG3 antibody, or antigen-binding portion thereof, such that an immune response to the antigen in the subject is enhanced. Preferably, the antibody is a human anti-human LAG3 antibody (such as any of the human anti-LAG3 antibodies described herein). The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Combination Therapy

A LAG3 binding polypeptide, e.g., an anti-LAG3 antibody or antibody fragment, can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

The disclosed human anti-LAG-3 antibodies can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Coadministration of the anti-LAG3 antibodies and antibody fragments of the invention, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

An anti-LAG3 antibody or antibody fragment as described herein, may be coadministered with one or more additional antibodies that are effective in stimulating immune responses to thereby further enhance, stimulate or upregulate immune responses in a subject. For example, the invention provides a method for stimulating an immune response in a subject comprising administering to the subject an anti-LAG3 antibody or antibody fragment and one or more additional immunostimulatory antibodies, such as an anti-PD-1 antibody, an anti-PD-L1 antibody and/or an anti-CTLA-4 antibody, such that an immune response is stimulated in the subject, for example to inhibit tumor growth or to stimulate an anti-viral response.

An important part of the immune system is its ability to distinguish between normal cells in the body and those it sees as "foreign." This lets the immune system attack the foreign cells while leaving the normal cells alone. To do this, it uses "checkpoints," which are molecules on certain immune cells that need to be activated (or inactivated) to start an immune response. Cancer cells sometimes find ways to use these checkpoints to avoid being attacked by the immune system. Accordingly, an immune checkpoint inhibitor includes a drug or agent, e.g., an antibody, that can activate T cells which are inactive in the absence of the drug or agent due, at least in part, to signaling from a cancer cell which can maintain the inactive state of the T cell.

Thus, in one embodiment, an anti-LAG3 antibody or antigen binding antibody fragment of the invention is used in combination with an immune checkpoint inhibitor for the treatment of cancer. For example, in one embodiment, an anti-LAG3 antibody, or antigen binding fragment, described herein is administered in combination with an antibody which is an immune checkpoint inhibitor, including, but not limited to, an anti-cytotoxic T-lymphocyte antigen 4 (CTLA-4) antibody, an anti-programmed death 1 (PD-1) antibody, or an anti-programmed death-ligand 1 (PD-L1) antibody. In one embodiment, an anti-LAG3 antibody, or antigen binding fragment, described herein is administered in combination with trastuzumab (Herceptin).

In one embodiment, the subject is administered an anti-LAG3 antibody or antibody fragment and an anti-PD-1 antibody. In another embodiment, the subject is administered an anti-LAG3 antibody or antibody fragment and an anti-PD-L1 antibody. In yet another embodiment, the subject is administered an anti-LAG-3 antibody or antibody fragment and an anti-CTLA-4 antibody.

In one embodiment, the invention provides a method for treating a hyperproliferative disease (e.g., cancer), comprising administering a LAG3 antibody and a CTLA-4 antibody to a subject. In further embodiments, the anti-LAG3 antibody is administered at a subtherapeutic dose, the anti-CTLA-4 antibody is administered at a subtherapeutic dose, or both are administered at a subtherapeutic dose. Alternatively, a method for altering an adverse event associated with treatment of a hyperproliferative disease with an immunostimulatory agent, comprising administering an anti-LAG3 antibody and a subtherapeutic dose of anti-CTLA-4 antibody to a subject. In one embodiment, an anti-LAG3 antibody, or antigen binding fragment, described herein is administered in combination with an anti-cytotoxic T-lymphocyte antigen 4 (CTLA-4) antibody, for example ipilimumab (YERVOY) or tremelimumab (CP-675,206; MedImmune).

Another combination comprises administering a LAG3 antibody or antibody fragment and a PD-1 or PD-L1 antibody to a subject. In one embodiment, an anti-LAG3 antibody, or antigen binding fragment, described herein is administered in combination with an anti-programmed death 1 (PD-1) antibody, for example pembrolizumab (KEYTRUDA) or nivolumab (OPDIVO). In one embodiment, an anti-LAG3 antibody, or antigen binding fragment, described herein is administered in combination with an anti-programmed death-ligand 1 (PD-L1) antibody, for example avelumab (MSB0010718C), atezolizumab (TECENTRIQ) or durvalumab (MEDI4736). In further embodiments, the anti-LAG-3 antibody is administered at a subtherapeutic dose, the anti-PD-1 or PD-L1 antibody is administered at a subtherapeutic dose, or both are administered at a subtherapeutic dose.

Blockade of LAG3 and one or more second target antigens such as CTLA-4 and/or PD-1 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-LAG3 antibodies.

Therapeutic Methods and Compositions

Suitable routes of administering the antibody compositions described herein (e.g., human monoclonal antibodies, multispecific and bispecific molecules and immunoconjugates) are in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.).

Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Preferably, the disclosed antibodies are administered by inhalation, but aerosolization of full IgG antibodies may prove limiting due to their molecular size (~150 kDa). To maximize available commercial aerosolization devices, smaller Fab fragments may be required.

In certain embodiments, the subject anti-LAG3 antibodies or antibody fragments of the invention can be used alone.

Diagnostics and Kits

In certain embodiments, the binding polypeptides, e.g., antibodies, or fragments thereof can be labeled or unlabeled for diagnostic purposes. Typically, diagnostic assays entail detecting the formation of a complex resulting from the binding of a binding polypeptide, e.g., an antibody, to LAG3. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides, e.g., antibodies or fragments thereof, can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides, e.g., antibodies or fragments thereof, of the present invention can be utilized in enzyme immunoassays, wherein the subject polypeptides are conjugated to an enzyme. When a biological sample comprising a LAG3 protein is combined with the subject binding polypeptides, binding occurs between the binding polypeptides and the LAG3 protein. In one embodiment, a sample containing cells expressing a LAG3 protein (e.g., endothelial cells) is combined with the subject antibodies, and binding occurs between the binding polypeptides and cells bearing a LAG3 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a LAG3 protein in a biological sample using the antibodies or fragments thereof of the invention can also be prepared. Such kits will include a LAG3 binding polypeptide, e.g., antibodies or fragments thereof, which binds to a LAG3 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin) For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

The invention is further described in the following examples, which are in not intended to limit the scope of the invention.

Example 1

A screen was performed to identify human anti-human LAG3 antibodies, the heavy and light chain variable amino acid sequences (including the CDRs thereof).

To determine the binding capability of various anti-LAG3 antibodies disclosed herein, T cells were cultured with magnetic beads coated with antibodies reactive with CD3 and CD28. After three days of culture a significant percentage of the cells expressed LAG3. The LAG3 expressing cells were incubated with the test antibodies (1 microgram per ml) followed by staining with a phycoerythrin labeled goat anti-human IgG antibody. Several antibodies had reactivity with the activated T cells and these are shown in FIG. 1.

Figure 2:
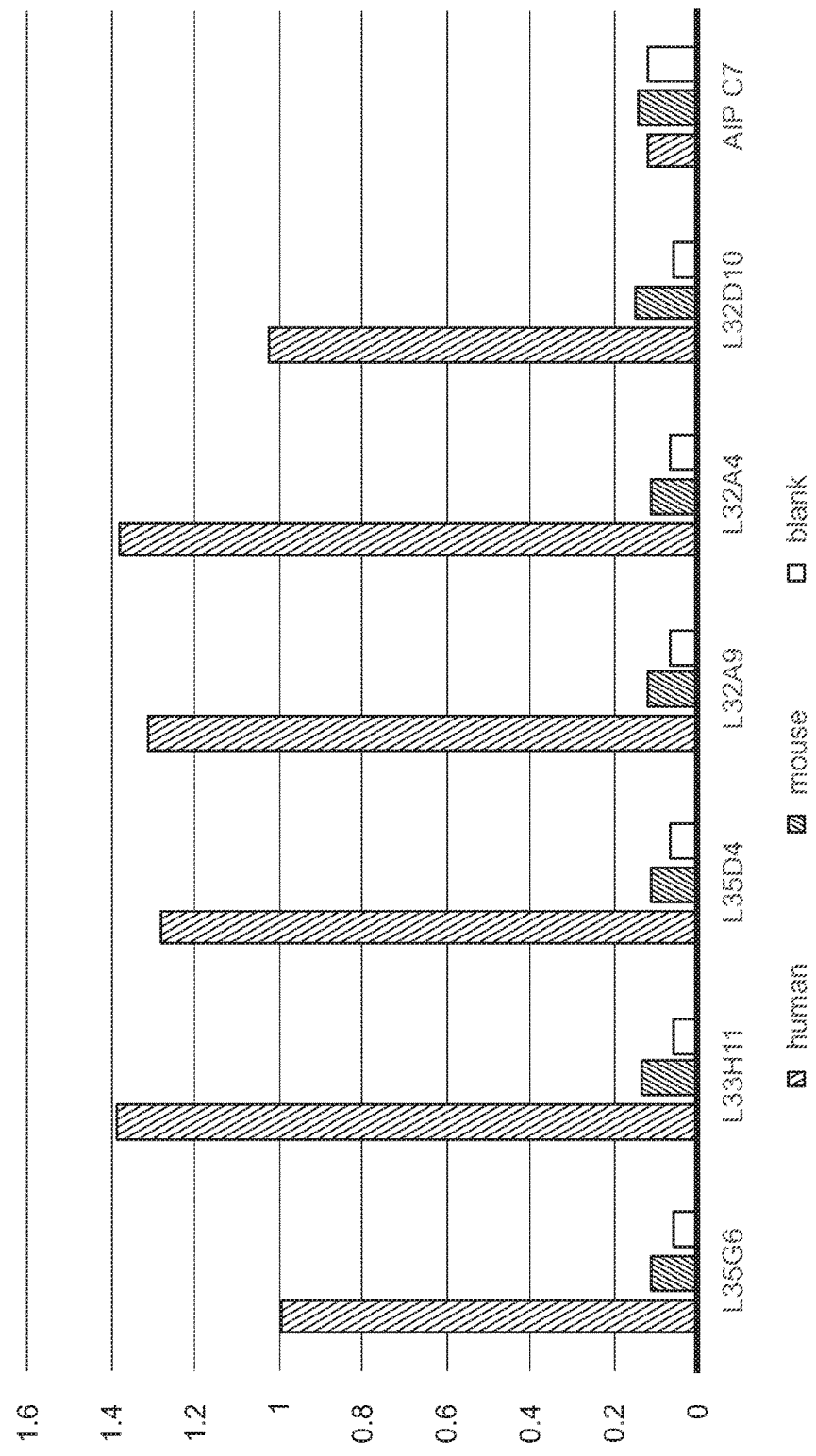
FIG. 2 is a graph that shows the cross-reactivity of anti-hLAG3 antibodies L35G6, L33H11, L35D4, L32A9, L32A4, and L32D10 to recombinant mouse LAG3 and human LAG3. Anti-AIP antibody C7 was used as a control.

An analysis of the cross-reactivity of various LAG3 antibodies to recombinant mouse LAG3 and human LAG3 was also performed. A Maxisorb ELISA plate was coated with 2 ug/mL recombinant human, and mouse LAG3/Fc (blank: PBS). Incubated overnight at 4° C. The plate was washed 3 times with PBS-Tween (PBST), then blocked with Casein blocking buffer for 1 hour at room temperature. Next, IgGs diluted in casein (about 5 ug/ml) were added, and incubated 30 min with shaking. The plate was washed 3 times with PBST. Horseradish peroxidase (HRP)-conjugated goat anti-human Lambda HRP (1:1000 in casein) was added, then 3,3',5,5'-Tetramethylbenzidine (TMB) was added as substrate and developed 30 min 2M H2SO4 was used to stop the reaction and the OD was read at 450 nm Anti-AIP antibody C7 was used as a control antibody. The results are provided in FIG. 2 and show that anti-LAG3 antibodies L35G6, L33H11, L35D4, L32A9, L32A4 and L32D10 bind to human but do not bind to mouse LAG3.

The binding affinity of antibody L3C5 for human LAG3 was also tested using a BiaCore assay. For antibody L3C5, $K_a$ was found to be 4.73 E5 (1/Ms), $K_d$ was found to be 0.0717 (1/s), $R^{max}$ was found to be 261(RU), $K_A$ was found to be 6.6 E6 (1/M), $K_D$ was found to be 1.52 E-7 (M) and chi2 was 3.65. Biacore was used to measure the affinity of LAG3 antibody L3C5. Anti-human Fc antibody (GE, BR-1008-39) was immobilized on CM5 sensor chip to approximately 5000 RU using standard NHS/EDC coupling methodology. Antibody (approximately 2 ug/ml) were captured for 60 s at a flow rate 10 uL/min. Recombinant human LAG3/His was serially diluted in running buffer (HBS-EP). All measurements were conducted with a flow rate of 30 µL/min Surfaces were regenerated with 3M MgCl2 (from human antibody kit) for 60 s. A 1:1 (Langmuir) binding model was used to fit the data.

Example 2

Figure 3:
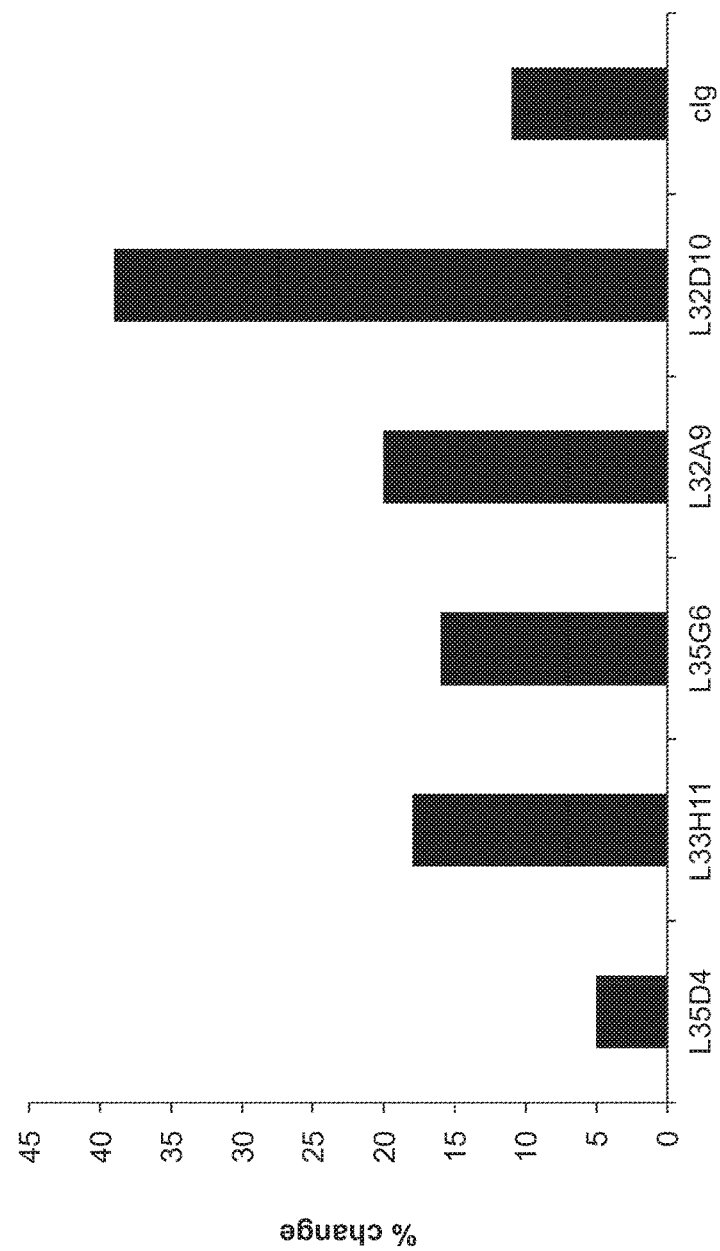
FIG. 3 shows results that determined the effect of anti-LAG3 antibodies on LAG3 expressing T cells. A percent change with respect to the medium control was calculated and is shown in FIG. 3. An isotype match IgG was used as a control (cIg).
Figure 4:
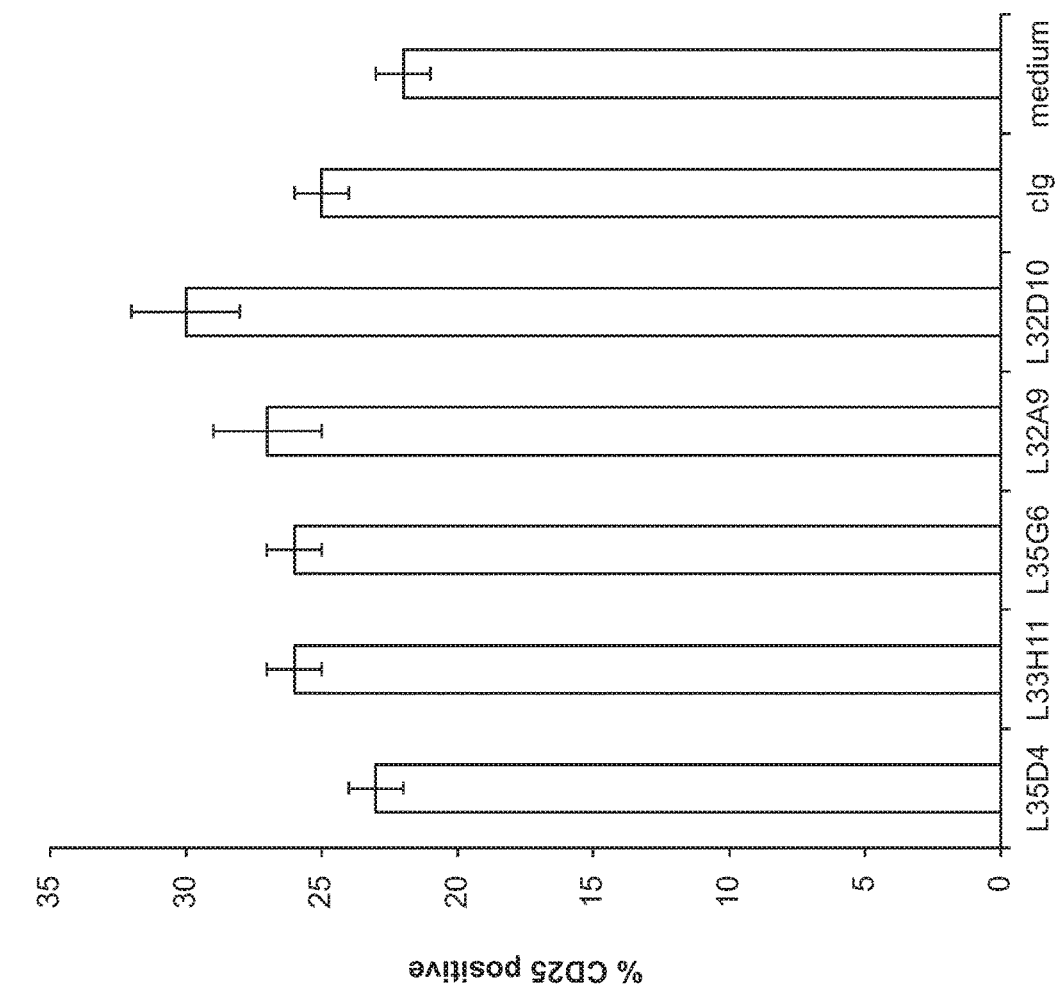
FIG. 4 provides a graph that shows the results of in vitro studies using mixed lymphocyte reactions (MLR) to measure T cell activation. Cells were assayed for CD25 expression as a measure of T cell activation (% CD25 positive).

Functional in vitro studies using a two-step activation protocol mixed lymphocyte reactions (MLR) to measure T cell activation were performed. The functional activity of the anti-LAG3 antibodies was evaluated by measuring their effect on the response of LAG3 expressing T cells to stimulation by the superantigen, staphylococcal enterotoxin B (SEB). T cells were cultured with magnetic beads coated with antibodies reactive with CD3 and CD28. The following day, the beads were removed and the cells were cultured in fresh medium. After a further two days the T cells were harvested and added to the wells of a flat bottom microtiter plate at a concentration of $1\times10^5$ cells per well. To these wells were added $2\times10^4$ freshly prepared B cells and SEB (10 ng/ml). After three days of culture the cells were stained for CD25 expression. To determine the effect of the anti-LAG3 antibodies, the percent change with respect to the medium control was calculated and is shown in FIG. 3. FIG. 4 shows the level of T cell activation, as measured by CD25 expression, in the presence of the anti-LAG3 antibodies. This data is expressed as a percent change from that of medium control and is shown in FIG. 3. FIGS. 3 and 4 together show that four out of the five anti-LAG3 antibodies tested augment T cell activation greater than that of control IgG. Thus, the antibodies were able to block LAG3 activity and promote T cell activation.

Example 3

Figure 5:
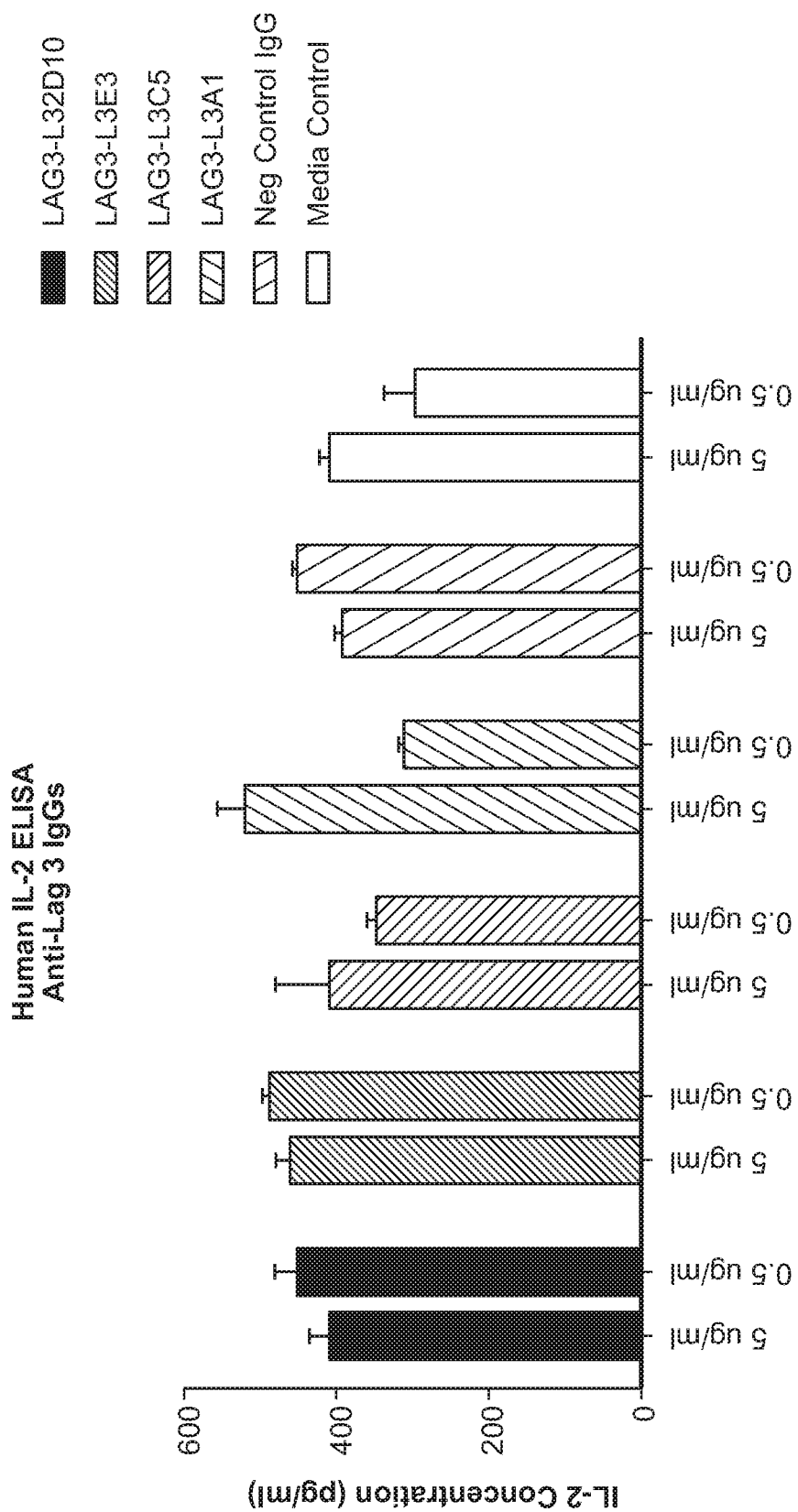
FIG. 5 is a graph that shows the results of an ELISA assay to determine the effect of anti-LAG3 antibodies L32D10, L3E3, L3C5 and L3A1 (at concentrations of 5 μg/ml and 0.5 μg/ml) on IL-2 cytokine production.
Figure 6:
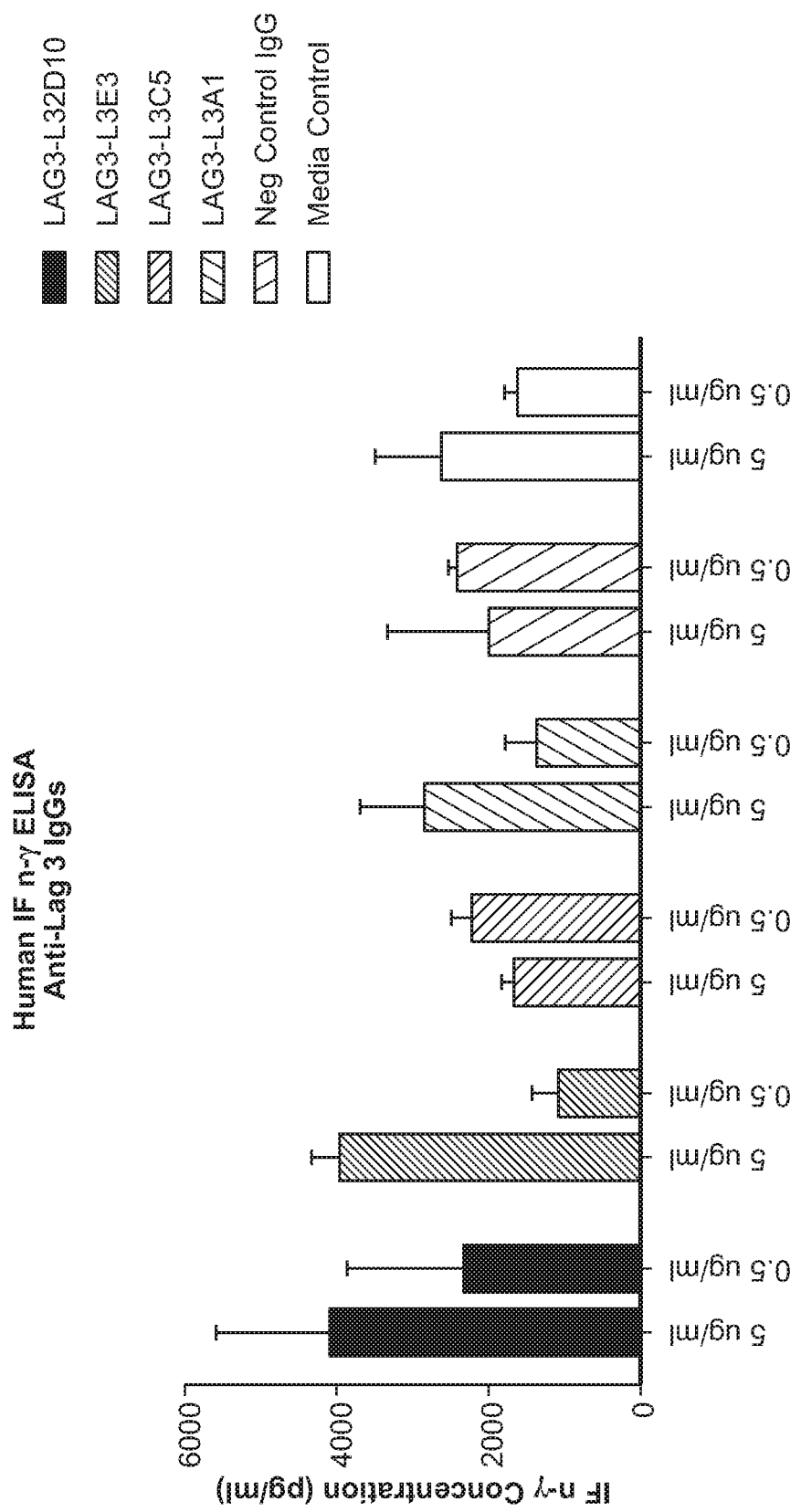
FIG. 6 is a graph that shows the results of an ELISA assay to determine the effect of anti-LAG3 antibodies L32D10, L3E3, L3C5 and L3A1 (at concentrations of 5 μg/ml and 0.5 μg/ml) on interferon gamma (IFNγ) cytokine production.

Functional in vitro studies using a mixed lymphocyte reactions (MLR) were performed to evaluate other anti-LAG3 antibodies, with cytokine production being the measure of T cell activation. An ELISA assay was carried out to determine the effect of anti-LAG3 antibodies L32D10, L3E3, L3C5 and L3A1 (at concentrations of 5 µg/ml and 0.5 µg/ml) on IL-2 and interferon gamma (IFNγ) cytokine production. IL-2 and IFNγ cytokine production are measures of T-cell activation. ELISA kits were purchased from Biolegend and were performed following the manufacturer's instructions. The results presented in FIG. 5 and FIG. 6 show that L32D10 and L3E3 augment the production of both IL-2 and interferon gamma (IFNγ), respectively, whereas clone L3A1 only augments IL-2 production. An IgG1 that does not bind to LAG3 and media only were used as controls.

It is understood that the examples and embodiments described herein are for illustrative purposes only and that various modifications or changes in light thereof will be suggested to persons skilled in the art and are to be included within the spirit and purview of the appended claims. All publications, patents, and patent applications cited herein are hereby incorporated by reference in their entirety for all purposes.

TABLE 3

| Sequence Listing | | |
|---|---|---|
| Binder | VH Heavy chain binding region | VL light chain binding region |
| L35D4 | QVQLVQSGAEVKKPGASVKVSCKASGY TFTSYYMHWVRQAPGQGLEWMGIINPS AGSTSYAQKFQGRVTMTRDTSTSTVYM | QSVLTQPPSASGSPGQSVTISCTGTS SDVGGYNYVSWYQQYPGKAPRLMIFE VTERASGVPDRFSGSKSGNTASLTVS |

TABLE 3-continued

Sequence Listing

| Binder | VH Heavy chain binding region | VL light chain binding region |
|---|---|---|
| | ELSSLRSEDTAVYYCARELMATGGFDY WGQGTLVTVSS SEQ ID NO. 1 | GLQTEDEAVYFCSSYSGSNNPGAMFG GGTKLTVL SEQ ID NO. 2 |
| L35D4 | HC CDR1: SYYMH SEQ ID NO. 15 HC CDR2: IINPSAGSTSYAQKFQG SEQ ID NO. 16 HC CDR3: ELMATGGFDY SEQ ID NO. 17 | LC CDR1: TGTSSDVGGYNYVS SEQ ID NO. 18 LC CDR2: EVTERAS SEQ ID NO. 19 LC CDR3: SSYSGSNNPGAM SEQ ID NO. 20 |
| L35G6 | QVQLVQSGAEVKKPGASVKVSCKASGY TFTSYYMHWVRQAPGQGLEWMGIINPS AGSTSYAQKFQGRVTMTRDTSTSTVYM ELSSLRSEDTAVYYCARELMATGGFDY WGQGTLVTVSS SEQ ID NO. 1 | QAGLTQPASVSGSPGQSITISCTGSS SDVGGYSYVSWYQKHPGKAPKLMIYD VTNRPSGVSNRFSGSKSGNTASLTIS GLQAEDEADYYCSTYTRSNTLVFGPG TKVTVL SEQ ID NO. 3 |
| L35G6 | HC CDR1: SYYMH SEQ ID NO. 15 HC CDR2: IINPSAGSTSYAQKFQG SEQ ID NO. 16 HC CDR3: ELMATGGFDY SEQ ID NO. 17 | HC CDR1: TGSSSDVGGYSYVS SEQ ID NO. 21 HC CDR2: DVTNRPS SEQ ID NO. 22 HC CDR3: STYTRSNTLV SEQ ID NO. 23 |
| L33H11 | QVQLVQSGAEVKKPGASVKVSCKASGY TFTSYYMHWVRQAPGQGLEWMGIINPS AGSTSYAQKFQGRVTMTRDTSTSTVYM ELSSLRSEDTAVYYCARELMATGGFDY WGQGTLVTVSS SEQ ID NO. 1 | LPVLTQPASVSGSPGQSITISCTGTS SDVGGYNYVSWYQQHPGKAPKLMIYD VTNRPSGVSNRFSGSKSGNTASLTIS GLQAEDEADYYCSSYTSSNTLLFGGG TQLTVL SEQ ID NO. 4 |
| L33H11 | HC CDR1: SYYMH SEQ ID NO. 15 HC CDR2: IINPSAGSTSYAQKFQG SEQ ID NO. 16 HC CDR3: ELMATGGFDY SEQ ID NO. 17 | HC CDR1: TGTSSDVGGYNYVS SEQ ID NO. 24 HC CDR2: DVTNRPS SEQ ID NO. 25 HC CDR3: SSYTSSNTLL SEQ ID NO. 26 |
| L32A9 | QVQLVQSGAEVKKPGASVKVSCKASGY TFTSYYMHWVRQAPGQGLEWMGIINPS AGSTSYAQKFQGRVTMTRDTSTSTVYM ELSSLRSEDTAVYYCARELMATGGFDY WGQGTLVTVSS SEQ ID NO. 1 | QSVVTQPPSVSAAPGQKVTISCSGSS SNIGNNYVSWYQQLPGTAPKLLIYDN NKRHSGIPDRFSGSTSDTSATLGITR LQTGDEADYYCGTWDSSLSAYVFGTG TKVTVL SEQ ID NO. 5 |
| L32A9 | HC CDR1: SYYMH SEQ ID NO. 15 HC CDR2: IINPSAGSTSYAQKFQG SEQ ID NO. 16 HC CDR3: ELMATGGFDY SEQ ID NO. 17 | HC CDR1: SGSSSNIGNNYVS SEQ ID NO. 27 HC CDR2: DNNKRHS SEQ ID NO. 28 HC CDR3: GTWDSSLSAYV SEQ ID NO. 29 |
| L32D10 | QVQLVQSGAEVKKPGASVKVSCKASGY TFTSYYMHWVRQAPGQGLEWMGIINPS AGSTSYAQKFQGRVTMTRDTSTSTVYM ELSSLRSEDTAVYYCARELMATGGFDY WGQGTLVTVSS SEQ ID NO. 1 | QSVLTQPPSASGSPGQSVTISCTGTS SDVGGYDYVSWYQQHQGKAPKLMIYD VSNRPSGVSNRFSGSKSGNTASLTIS GLQAEDEADYYCSSYTSSTTLVFGGG TKLTVL SEQ ID NO. 6 |
| L32D10 | HC CDR1: SYYMH SEQ ID NO. 15 HC CDR2: IINPSAGSTSYAQKFQG SEQ ID NO. 16 HC CDR3: ELMATGGFDY SEQ ID NO. 17 | HC CDR1: TGTSSDVGGYDYVS SEQ ID NO. 30 HC CDR2: DVSNRPS SEQ ID NO. 31 HC CDR3: SSYTSSTTLV SEQ ID NO. 32 |
| L32A4 | QVQLVQSGAEVKKPGASVKVSCKASGY TFTSYYMHWVRQAPGQGLEWMGIINPS AGSTSYAQKFQGRVTMTRDTSTSTVYM ELSSLRSEDTAVYYCARELMATGGFDY WGQGTLVTVSS SEQ ID NO. 1 | QSVLTQPASVSGSPGQSITISCTGTS SDIGAYNFVSWYQQHPGKAPKLMIYG VSNRPSGVSSRFSGSKSGSTASLTIS GLQAEDEADYYCSSYTTSGSAVFGTG TKLTVL SEQ ID NO. 7 |
| L32A4 | HC CDR1: SYYMH SEQ ID NO. 15 HC CDR2: IINPSAGSTSYAQKFQG SEQ ID NO. 16 HC CDR3: ELMATGGFDY SEQ ID NO. 17 | HC CDR1: TGTSSDIGAYNFVS SEQ ID NO. 33 HC CDR2: GVSNRPS SEQ ID NO. 34 HC CDR3: SSYTTSGSAV SEQ ID NO. 35 |

TABLE 3-continued

Sequence Listing

| Binder | VH Heavy chain binding region | VL light chain binding region |
|---|---|---|
| L3A1 | EVQLLESGAEVKKPGASVKVSCKASGY TFTSYYMHWVRQAPGQGLEWMGIINPS AGSTSYAQKFQGRVTMTRDTSTSTVYM ELSSLRSEDTAVYYCARELMATGGFDY WGQGTLVTVSS SEQ ID NO. 8 | QSVLTQPASVSGSPGQSITISCTGTS SDIGAYNFVSWYQQHPGKAPKLMIYG VSNRPSGVSSRFSGSKSGSTASLTIT GLQAEDEADYYCSSYTTSGSAVFGTG TKLTVL SEQ ID NO. 9 |
| L3A1 | HC CDR1: SYYMH SEQ ID NO. 36 HC CDR2: IINPSAGSTSYAQKFQG SEQ ID NO. 37 HC CDR3: ELMATGGFDY SEQ ID NO. 38 | HC CDR1: TGTSSDIGAYNFVS SEQ ID NO. 39 HC CDR2: GVSNRPS SEQ ID NO. 40 HC CDR3: SSYTTSGSAV SEQ ID NO. 41 |
| L3A10 | EVQLLESGGGVVQPGRSLRVSCAASGF TFSNHAMHWVRQAPGKGLEWVAVISYD GSKKFYSDSVRGRFTISRDNSKNTLYL QMNSLRPEDTAVYYCAKGAHGYTSGWH DYWGQGTLVTVSS SEQ ID NO. 10 | DVVMTQSPSSLSASVGDRVSITCRAS QNIGRYLNWYQQKPGKAPKLLVSAAS SLQGGVPSRFSGSGSGTDFTLTISRL QPEDFATYFCQQTYSSPQCTFGQGTK VDIK SEQ ID NO. 11 |
| L3A10 | HC CDR1: NHAMH SEQ ID NO. 42 HC CDR2: VISYDGSKKFYSDSVRG SEQ ID NO. 43 HC CDR3: GAHGYTSGWHDY SEQ ID NO. 44 | HC CDR1: RASQNIGRYLN SEQ ID NO. 45 HC CDR2: AASSLQG SEQ ID NO. 46 HC CDR3: QQTYSSPQCT SEQ ID NO. 47 |
| L3C5 | QVQLVQSGSELKKPGASVKVSCKASGY TFTNYYMHWVRQAPGQGLEWMGIINPS GGATNYAQKFQGRVTMTRDTSTSTVYM ELSSLRSEDTAVYYCARDSGYDLGYGM DVWGQGTLVTVSS SEQ ID NO. 12 | QSVLTQPASVSGSPGQSITISCTGTS SDVGGYNYVSWYQQHPGKAPKLMIYD VSNRPSGASNRFSGSKSGNTASLTIS GLQAEDEADYYCSSYTNRNTLLFGGG TKLTVL SEQ ID NO. 13 |
| L3C5 | HC CDR1: NYYMH SEQ ID NO. 48 HC CDR2: IINPSGGATNYAQKFQG SEQ ID NO. 49 HC CDR3: DSGYDLGYGMDV SEQ ID NO. 50 | HC CDR1: TGTSSDVGGYNYVS SEQ ID NO. 51 HC CDR2: DVSNRPS SEQ ID NO. 52 HC CDR3: SSYTNRNTLL SEQ ID NO. 53 |
| L3E3 | EVQLLESGAEVKKPGASVKVSCKASGY TFTSYYMHWVRQAPGQGLEWMGIINPS AGSTSYAQKFQGRVTMTRDTSTSTVYM ELSSLRSEDTAVYYCARELMATGGFDY WGQGTLVTVSS SEQ ID NO. 8 | QSVLTQPASASGSPGQSITISCTGTS SDVGGYNYVSWYQQHPGKAPKLMIYD VSNRPSGVSNRFSGSKSGNTASLTIS GLQAEDEANYYCSSYTSSSTNVFGTG TKVTVL SEQ ID NO. 14 |
| L3E3 | HC CDR1: SYYMH SEQ ID NO. 36 HC CDR2: IINPSAGSTSYAQKFQG SEQ ID NO. 37 HC CDR3: ELMATGGFDY SEQ ID NO. 38 | HC CDR1: TGTSSDVGGYNYVS SEQ ID NO. 54 HC CDR2: DVSNRPS SEQ ID NO. 55 HC CDR3: SSYTSSSTNV SEQ ID NO. 56 |

We claim:

1. An isolated anti-human LAG3 (hLAG3) antibody, or an antigen-binding fragment thereof, comprising
   a heavy chain variable domain comprising a heavy chain CDR set (CDR1, CDR2, and CDR3) as set forth in SEQ ID Nos: 36, 37, and 38; and
   a light chain variable domain comprising a light chain CDR set (CDR1, CDR2, and CDR3) as set forth in SEQ ID Nos: 54, 55, and 56.

2. The anti-hLAG3 antibody, or the antigen-binding fragment thereof, of claim 1, wherein the heavy chain variable domain comprises the amino acid sequence that is at least 95% identical to SEQ ID NO. 8, and wherein the light chain variable domain comprises the amino acid sequence that is at least 95% identical to SEQ ID NO. 14.

3. The anti-hLAG3 antibody, or the antigen-binding fragment thereof, of claim 1, wherein the heavy chain variable domain comprises the amino acid sequence set forth in SEQ ID NO. 8; and wherein the light chain variable domain comprises the amino acid sequence set forth in SEQ ID NO. 14.

4. The anti-hLAG antibody, or the antigen binding fragment thereof, of claim 1, wherein the antibody has a $K_D$ of at least $1 \times 10^{-6}$ M.

5. The anti-hLAG3 antibody, or the antigen-binding fragment thereof, of claim 1, wherein the antibody is an IgG, an IgM, an IgD, an IgA, or an IgE.

6. The anti-hLAG3 antibody, or the antigen-binding fragment thereof, of claim 5, wherein the antibody is an IgG1 or an IgG4 isotype.

7. A pharmaceutical composition comprising the anti-hLAG3 antibody, or the antigen binding fragment thereof of claim 1, and a pharmaceutically acceptable carrier.

8. The anti-hLAG3 antibody, or the antigen-binding fragment thereof, of claim 1, wherein the antibody, or the antigen-binding fragment thereof, is a monoclonal antibody, a human antibody, a humanized antibody, an Fab, an Fab', an F(ab')2, an Fv, a domain antibody (dAb), a single-chain antibody (scFv), a chimeric antibody, a diabody, a triabody or a tetrabody.

9. The anti-hLAG3 antibody, or the antigen-binding fragment thereof, of claim 2, wherein the antibody, or the antigen-binding fragment thereof, is a monoclonal antibody, a human antibody, a humanized antibody, an Fab, an Fab', an F(ab')2, an Fv, a domain dAb, an scFv, a chimeric antibody, a diabody, a triabody or a tetrabody.

10. The anti-hLAG3 antibody, or the antigen-binding fragment thereof, of claim 3, wherein the antibody, or the antigen-binding fragment thereof, is a monoclonal antibody, a human antibody, a humanized antibody, an Fab, an Fab', an F(ab')2, an Fv, a domain dAb, an scFv, a chimeric antibody, a diabody, a triabody or a tetrabody.

* * * * *

SEQUENCE LISTING

<160> NUMBER OF SEQ ID NOS: 56

<210> SEQ ID NO 1
<211> LENGTH: 119
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
                20                  25                  30

Tyr Met His Trp Val Arg Gln Ala Pro Gly Gln Gly Leu Glu Trp Met
         35                  40                  45

Gly Ile Ile Asn Pro Ser Ala Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                 85                  90                  95

Ala Arg Glu Leu Met Ala Thr Gly Gly Phe Asp Tyr Trp Gly Gln Gly
                100                 105                 110

Thr Leu Val Thr Val Ser Ser
            115

<210> SEQ ID NO 2
<211> LENGTH: 112
<212> TYPE: PRT
<213> ORGANISM: Homo sapiens

<400> SEQUENCE: 2

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln Tyr Pro Gly Lys Ala Pro Arg Leu
            35                  40                  45

Met Ile Phe Glu Val Thr Glu Arg Ala Ser Gly Val Pro Asp Arg Phe
 50                  55                  60

Ser Gly Ser Lys Ser Gly Asn Thr Ala Ser Leu Thr Val Ser Gly Leu
65                  70                  75                  80

Gln Thr Glu Asp Glu Ala Val Tyr Phe Cys Ser Ser Tyr Ser Gly Ser
                 85                  90                  95

Asn Asn Pro Gly Ala Met Phe Gly Gly Gly Thr Lys Leu Thr Val Leu
                100                 105                 110

<210> SEQ ID NO 3
<211> LENGTH: 110
<212> TYPE: PRT
<213> ORGANISM: Homo sapiens

<400> SEQUENCE: 3

Gln Ala Gly Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
                20                  25                  30

Ser Tyr Val Ser Trp Tyr Gln Lys His Pro Gly Lys Ala Pro Lys Leu
            35                  40                  45

Met Ile Tyr Asp Val Thr Asn Arg Pro Ser Gly Val Ser Asn Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Thr Tyr Thr Arg Ser
                 85                  90                  95

Asn Thr Leu Val Phe Gly Pro Gly Thr Lys Val Thr Val Leu
                100                 105                 110
```

-continued

<210> SEQ ID NO 4
<211> LENGTH: 110
<212> TYPE: PRT
<213> ORGANISM: Homo sapiens

<400> SEQUENCE: 4

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Asn Thr Leu Leu Phe Gly Gly Gly Thr Gln Leu Thr Val Leu
            100                 105                 110

<210> SEQ ID NO 5
<211> LENGTH: 110
<212> TYPE: PRT
<213> ORGANISM: Homo sapiens

<400> SEQUENCE: 5

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg His Ser Gly Ile Pro Asp Arg Phe Ser
    50                  55                  60

Gly Ser Thr Ser Asp Thr Ser Ala Thr Leu Gly Ile Thr Arg Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val Leu
            100                 105                 110

<210> SEQ ID NO 6
<211> LENGTH: 110
<212> TYPE: PRT
<213> ORGANISM: Homo sapiens

<400> SEQUENCE: 6

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asp Tyr Val Ser Trp Tyr Gln Gln His Gln Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Cys Ser Ser Tyr Thr Ser Ser
                85                  90                  95

Thr Thr Leu Val Phe Gly Gly Gly Thr Lys Leu Thr Val Leu
            100                 105                 110

<210> SEQ ID NO 7
<211> LENGTH: 110
<212> TYPE: PRT
<213> ORGANISM: Homo sapiens

<400> SEQUENCE: 7

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ala Tyr
            20                  25                  30

Asn Phe Val Ser Trp Tyr Gln Gln His Pro Gly Lys Ala Pro Lys Leu
        35                  40                  45

Met Ile Tyr Gly Val Ser Asn Arg Pro Ser Gly Val Ser Ser Arg Phe
    50                  55                  60

Ser Gly Ser Lys Ser Gly Ser Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Gly Ser Ala Val Phe Gly Thr Gly Thr Lys Leu Thr Val Leu
            100                 105                 110

<210> SEQ ID NO 8
<211> LENGTH: 119
<212> TYPE: PRT
<213> ORGANISM: Homo sapiens

<400> SEQUENCE: 8

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Ala Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Leu Met Ala Thr Gly Gly Phe Asp Tyr Trp Gly Gln Gly
            100                 105                 110

Thr Leu Val Thr Val Ser Ser
        115

<210> SEQ ID NO 9
<211> LENGTH: 110
<212> TYPE: PRT
<213> ORGANISM: Homo sapiens

<400> SEQUENCE: 9

Gln Ser Val Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Ile Gly Ala Tyr
                20                  25                  30

Asn Phe Val Ser Trp Tyr Gln Gln His Pro Gly Lys Ala Pro Lys Leu
            35                  40                  45

Met Ile Tyr Gly Val Ser Asn Arg Pro Ser Gly Val Ser Ser Arg Phe
        50                  55                  60

Ser Gly Ser Lys Ser Gly Ser Thr Ala Ser Leu Thr Ile Thr Gly Leu
65                  70                  75                  80

Gln Ala Glu Asp Glu Ala Asp Tyr Tyr Cys Ser Ser Tyr Thr Thr Ser
                85                  90                  95

Gly Ser Ala Val Phe Gly Thr Gly Thr Lys Leu Thr Val Leu
            100                 105                 110

<210> SEQ ID NO 10
<211> LENGTH: 121
<212> TYPE: PRT
<213> ORGANISM: Homo sapiens

<400> SEQUENCE: 10

Glu Val Gln Leu Leu Glu Ser Gly Gly Gly Val Val Gln Pro Gly Arg
1               5                   10                  15

Ser Leu Arg Val Ser Cys Ala Ala Ser Gly Phe Thr Phe Ser Asn His
                20                  25                  30

Ala Met His Trp Val Arg Gln Ala Pro Gly Lys Gly Leu Glu Trp Val
            35                  40                  45

Ala Val Ile Ser Tyr Asp Gly Ser Lys Lys Phe Tyr Ser Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Gly Ala His Gly Tyr Thr Ser Gly Trp His Asp Tyr Trp Gly
            100                 105                 110

Gln Gly Thr Leu Val Thr Val Ser Ser
        115                 120

<210> SEQ ID NO 11
<211> LENGTH: 108
<212> TYPE: PRT
<213> ORGANISM: Homo sapiens

<400> SEQUENCE: 11

Asp Val Val Met Thr Gln Ser Pro Ser Ser Leu Ser Ala Ser Val Gly
1               5                   10                  15

Asp Arg Val Ser Ile Thr Cys Arg Ala Ser Gln Asn Ile Gly Arg Tyr
                20                  25                  30

Leu Asn Trp Tyr Gln Gln Lys Pro Gly Lys Ala Pro Lys Leu Leu Val
            35                  40                  45

Ser Ala Ala Ser Ser Leu Gln Gly Gly Val Pro Ser Arg Phe Ser Gly
        50                  55                  60

Ser Gly Ser Gly Thr Asp Phe Thr Leu Thr Ile Ser Arg Leu Gln Pro
65                  70                  75                  80

Glu Asp Phe Ala Thr Tyr Phe Cys Gln Gln Thr Tyr Ser Ser Pro Gln
                85                  90                  95

Cys Thr Phe Gly Gln Gly Thr Lys Val Asp Ile Lys
            100                 105
```

```
<210> SEQ ID NO 12
<211> LENGTH: 121
<212> TYPE: PRT
<213> ORGANISM: Homo sapiens

<400> SEQUENCE: 12

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ala Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Tyr Asp Leu Gly Tyr Gly Met Asp Val Trp Gly
            100                 105                 110

Gln Gly Thr Leu Val Thr Val Ser Ser
        115                 120

<210> SEQ ID NO 13
<211> LENGTH: 110
<212> TYPE: PRT
<213> ORGANISM: Homo sapiens

<400> SEQUENCE: 13

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Ala Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asn Arg
                85                  90                  95

Asn Thr Leu Leu Phe Gly Gly Gly Thr Lys Leu Thr Val Leu
            100                 105                 110

<210> SEQ ID NO 14
<211> LENGTH: 110
<212> TYPE: PRT
<213> ORGANISM: Homo sapiens

<400> SEQUENCE: 14

Gln Ser Val Leu Thr Gln Pro Ala Ser Ala Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
```

```
                    50                  55                  60
Ser Gly Ser Lys Ser Gly Asn Thr Ala Ser Leu Thr Ile Ser Gly Leu
 65                  70                  75                  80

Gln Ala Glu Asp Glu Ala Asn Tyr Tyr Cys Ser Ser Tyr Thr Ser Ser
                     85                  90                  95

Ser Thr Asn Val Phe Gly Thr Gly Thr Lys Val Thr Val Leu
                100                 105                 110

<210> SEQ ID NO 15
<211> LENGTH: 5
<212> TYPE: PRT
<213> ORGANISM: Homo sapiens

<400> SEQUENCE: 15

Ser Tyr Tyr Met His
 1               5

<210> SEQ ID NO 16
<211> LENGTH: 17
<212> TYPE: PRT
<213> ORGANISM: Homo sapiens

<400> SEQUENCE: 16

Ile Ile Asn Pro Ser Ala Gly Ser Thr Ser Tyr Ala Gln Lys Phe Gln
 1               5                  10                  15

Gly

<210> SEQ ID NO 17
<211> LENGTH: 10
<212> TYPE: PRT
<213> ORGANISM: Homo sapiens

<400> SEQUENCE: 17

Glu Leu Met Ala Thr Gly Gly Phe Asp Tyr
 1               5                  10

<210> SEQ ID NO 18
<211> LENGTH: 14
<212> TYPE: PRT
<213> ORGANISM: Homo sapiens

<400> SEQUENCE: 18

Thr Gly Thr Ser Ser Asp Val Gly Gly Tyr Asn Tyr Val Ser
 1               5                  10

<210> SEQ ID NO 19
<211> LENGTH: 7
<212> TYPE: PRT
<213> ORGANISM: Homo sapiens

<400> SEQUENCE: 19

Glu Val Thr Glu Arg Ala Ser
 1               5

<210> SEQ ID NO 20
<211> LENGTH: 12
<212> TYPE: PRT
<213> ORGANISM: Homo sapiens

<400> SEQUENCE: 20

Ser Ser Tyr Ser Gly Ser Asn Asn Pro Gly Ala Met
 1               5                  10
```

<210> SEQ ID NO 21
<211> LENGTH: 14
<212> TYPE: PRT
<213> ORGANISM: Homo sapiens

<400> SEQUENCE: 21

Thr Gly Ser Ser Ser Asp Val Gly Gly Tyr Ser Tyr Val Ser
1               5                   10

<210> SEQ ID NO 22
<211> LENGTH: 7
<212> TYPE: PRT
<213> ORGANISM: Homo sapiens

<400> SEQUENCE: 22

Asp Val Thr Asn Arg Pro Ser
1               5

<210> SEQ ID NO 23
<211> LENGTH: 10
<212> TYPE: PRT
<213> ORGANISM: Homo sapiens

<400> SEQUENCE: 23

Ser Thr Tyr Thr Arg Ser Asn Thr Leu Val
1               5                   10

<210> SEQ ID NO 24
<211> LENGTH: 14
<212> TYPE: PRT
<213> ORGANISM: Homo sapiens

<400> SEQUENCE: 24

Thr Gly Thr Ser Ser Asp Val Gly Gly Tyr Asn Tyr Val Ser
1               5                   10

<210> SEQ ID NO 25
<211> LENGTH: 7
<212> TYPE: PRT
<213> ORGANISM: Homo sapiens

<400> SEQUENCE: 25

Asp Val Thr Asn Arg Pro Ser
1               5

<210> SEQ ID NO 26
<211> LENGTH: 10
<212> TYPE: PRT
<213> ORGANISM: Homo sapiens

<400> SEQUENCE: 26

Ser Ser Tyr Thr Ser Ser Asn Thr Leu Leu
1               5                   10

<210> SEQ ID NO 27
<211> LENGTH: 13
<212> TYPE: PRT
<213> ORGANISM: Homo sapiens

<400> SEQUENCE: 27

Ser Gly Ser Ser Ser Asn Ile Gly Asn Asn Tyr Val Ser
1               5                   10

<210> SEQ ID NO 28

```
<211> LENGTH: 7
<212> TYPE: PRT
<213> ORGANISM: Homo sapiens

<400> SEQUENCE: 28

Asp Asn Asn Lys Arg His Ser
1               5

<210> SEQ ID NO 29
<211> LENGTH: 11
<212> TYPE: PRT
<213> ORGANISM: Homo sapiens

<400> SEQUENCE: 29

Gly Thr Trp Asp Ser Ser Leu Ser Ala Tyr Val
1               5                   10

<210> SEQ ID NO 30
<211> LENGTH: 14
<212> TYPE: PRT
<213> ORGANISM: Homo sapiens

<400> SEQUENCE: 30

Thr Gly Thr Ser Ser Asp Val Gly Gly Tyr Asp Tyr Val Ser
1               5                   10

<210> SEQ ID NO 31
<211> LENGTH: 7
<212> TYPE: PRT
<213> ORGANISM: Homo sapiens

<400> SEQUENCE: 31

Asp Val Ser Asn Arg Pro Ser
1               5

<210> SEQ ID NO 32
<211> LENGTH: 10
<212> TYPE: PRT
<213> ORGANISM: Homo sapiens

<400> SEQUENCE: 32

Ser Ser Tyr Thr Ser Ser Thr Thr Leu Val
1               5                   10

<210> SEQ ID NO 33
<211> LENGTH: 14
<212> TYPE: PRT
<213> ORGANISM: Homo sapiens

<400> SEQUENCE: 33

Thr Gly Thr Ser Ser Asp Ile Gly Ala Tyr Asn Phe Val Ser
1               5                   10

<210> SEQ ID NO 34
<211> LENGTH: 7
<212> TYPE: PRT
<213> ORGANISM: Homo sapiens

<400> SEQUENCE: 34

Gly Val Ser Asn Arg Pro Ser
1               5

<210> SEQ ID NO 35
<211> LENGTH: 10
<212> TYPE: PRT
```

```
<213> ORGANISM: Homo sapiens

<400> SEQUENCE: 35

Ser Ser Tyr Thr Thr Ser Gly Ser Ala Val
1               5                   10

<210> SEQ ID NO 36
<211> LENGTH: 5
<212> TYPE: PRT
<213> ORGANISM: Homo sapiens

<400> SEQUENCE: 36

Ser Tyr Tyr Met His
1               5

<210> SEQ ID NO 37
<211> LENGTH: 17
<212> TYPE: PRT
<213> ORGANISM: Homo sapiens

<400> SEQUENCE: 37

Ile Ile Asn Pro Ser Ala Gly Ser Thr Ser Tyr Ala Gln Lys Phe Gln
1               5                   10                  15

Gly

<210> SEQ ID NO 38
<211> LENGTH: 10
<212> TYPE: PRT
<213> ORGANISM: Homo sapiens

<400> SEQUENCE: 38

Glu Leu Met Ala Thr Gly Gly Phe Asp Tyr
1               5                   10

<210> SEQ ID NO 39
<211> LENGTH: 14
<212> TYPE: PRT
<213> ORGANISM: Homo sapiens

<400> SEQUENCE: 39

Thr Gly Thr Ser Ser Asp Ile Gly Ala Tyr Asn Phe Val Ser
1               5                   10

<210> SEQ ID NO 40
<211> LENGTH: 7
<212> TYPE: PRT
<213> ORGANISM: Homo sapiens

<400> SEQUENCE: 40

Gly Val Ser Asn Arg Pro Ser
1               5

<210> SEQ ID NO 41
<211> LENGTH: 10
<212> TYPE: PRT
<213> ORGANISM: Homo sapiens

<400> SEQUENCE: 41

Ser Ser Tyr Thr Thr Ser Gly Ser Ala Val
1               5                   10

<210> SEQ ID NO 42
<211> LENGTH: 5
<212> TYPE: PRT
```

```
<213> ORGANISM: Homo sapiens

<400> SEQUENCE: 42

Asn His Ala Met His
1               5

<210> SEQ ID NO 43
<211> LENGTH: 17
<212> TYPE: PRT
<213> ORGANISM: Homo sapiens

<400> SEQUENCE: 43

Val Ile Ser Tyr Asp Gly Ser Lys Lys Phe Tyr Ser Asp Ser Val Arg
1               5                   10                  15

Gly

<210> SEQ ID NO 44
<211> LENGTH: 12
<212> TYPE: PRT
<213> ORGANISM: Homo sapiens

<400> SEQUENCE: 44

Gly Ala His Gly Tyr Thr Ser Gly Trp His Asp Tyr
1               5                   10

<210> SEQ ID NO 45
<211> LENGTH: 11
<212> TYPE: PRT
<213> ORGANISM: Homo sapiens

<400> SEQUENCE: 45

Arg Ala Ser Gln Asn Ile Gly Arg Tyr Leu Asn
1               5                   10

<210> SEQ ID NO 46
<211> LENGTH: 7
<212> TYPE: PRT
<213> ORGANISM: Homo sapiens

<400> SEQUENCE: 46

Ala Ala Ser Ser Leu Gln Gly
1               5

<210> SEQ ID NO 47
<211> LENGTH: 10
<212> TYPE: PRT
<213> ORGANISM: Homo sapiens

<400> SEQUENCE: 47

Gln Gln Thr Tyr Ser Ser Pro Gln Cys Thr
1               5                   10

<210> SEQ ID NO 48
<211> LENGTH: 5
<212> TYPE: PRT
<213> ORGANISM: Homo sapiens

<400> SEQUENCE: 48

Asn Tyr Tyr Met His
1               5

<210> SEQ ID NO 49
<211> LENGTH: 17
<212> TYPE: PRT
```

-continued

<213> ORGANISM: Homo sapiens

<400> SEQUENCE: 49

Ile Ile Asn Pro Ser Gly Gly Ala Thr Asn Tyr Ala Gln Lys Phe Gln
1               5                   10                  15
Gly

<210> SEQ ID NO 50
<211> LENGTH: 12
<212> TYPE: PRT
<213> ORGANISM: Homo sapiens

<400> SEQUENCE: 50

Asp Ser Gly Tyr Asp Leu Gly Tyr Gly Met Asp Val
1               5                   10

<210> SEQ ID NO 51
<211> LENGTH: 14
<212> TYPE: PRT
<213> ORGANISM: Homo sapiens

<400> SEQUENCE: 51

Thr Gly Thr Ser Ser Asp Val Gly Gly Tyr Asn Tyr Val Ser
1               5                   10

<210> SEQ ID NO 52
<211> LENGTH: 7
<212> TYPE: PRT
<213> ORGANISM: Homo sapiens

<400> SEQUENCE: 52

Asp Val Ser Asn Arg Pro Ser
1               5

<210> SEQ ID NO 53
<211> LENGTH: 10
<212> TYPE: PRT
<213> ORGANISM: Homo sapiens

<400> SEQUENCE: 53

Ser Ser Tyr Thr Asn Arg Asn Thr Leu Leu
1               5                   10

<210> SEQ ID NO 54
<211> LENGTH: 14
<212> TYPE: PRT
<213> ORGANISM: Homo sapiens

<400> SEQUENCE: 54

Thr Gly Thr Ser Ser Asp Val Gly Gly Tyr Asn Tyr Val Ser
1               5                   10

<210> SEQ ID NO 55
<211> LENGTH: 7
<212> TYPE: PRT
<213> ORGANISM: Homo sapiens

<400> SEQUENCE: 55

Asp Val Ser Asn Arg Pro Ser
1               5

<210> SEQ ID NO 56
<211> LENGTH: 10
<212> TYPE: PRT

```
<213> ORGANISM: Homo sapiens

<400> SEQUENCE: 56

Ser Ser Tyr Thr Ser Ser Ser Thr Asn Val
1               5                   10
```